(12) United States Patent
Verity

(10) Patent No.: US 8,153,661 B2
(45) Date of Patent: *Apr. 10, 2012

(54) CONTROLLED DELIVERY SYSTEM

(75) Inventor: A. Neil Verity, Sunnyvale, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/888,648

(22) Filed: Jul. 31, 2007

(65) Prior Publication Data

US 2008/0167630 A1 Jul. 10, 2008

Related U.S. Application Data

(63) Continuation of application No. 11/663,125, filed as application No. PCT/US2005/032863 on Sep. 15, 2005.

(60) Provisional application No. 60/610,797, filed on Sep. 17, 2004, provisional application No. 60/691,395, filed on Jun. 17, 2005.

(51) Int. Cl.
*A01N 37/08* (2006.01)
*A61K 31/215* (2006.01)
*A61F 2/00* (2006.01)

(52) U.S. Cl. ........................................ 514/330; 424/426

(58) Field of Classification Search .................. 514/330
See application file for complete search history.

(56) References Cited

U.S. PATENT DOCUMENTS

| | | | |
|---|---|---|---|
| 2,931,802 A | 4/1960 | Touey et al. |
| 3,743,398 A | 7/1973 | Johnson et al. |
| 3,853,837 A | 12/1974 | Fujino et al. |
| 3,992,365 A | 11/1976 | Beddell et al. |
| 4,024,248 A | 5/1977 | Konig et al. |
| 4,100,274 A | 7/1978 | Dutta et al. |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,487,603 A | 12/1984 | Harris |
| 4,530,840 A | 7/1985 | Tice et al. |
| 4,622,219 A | 11/1986 | Haynes |
| 4,692,147 A | 9/1987 | Duggan |
| 4,725,442 A | 2/1988 | Haynes |
| 4,725,852 A | 2/1988 | Gamblin et al. |
| 4,767,628 A | 8/1988 | Hutchinson |
| 4,795,641 A | 1/1989 | Kashdan |
| 4,834,984 A | 5/1989 | Goldie et al. |
| 4,844,909 A | 7/1989 | Goldie et al. |
| 4,861,598 A | 8/1989 | Oshlack |
| 4,891,225 A | 1/1990 | Langer et al. |
| 4,906,474 A | 3/1990 | Langer et al. |
| 4,938,763 A | 7/1990 | Dunn et al. |
| 4,957,744 A | 9/1990 | della Valle et al. |
| 4,970,075 A | 11/1990 | Oshlack |
| 4,990,341 A | 2/1991 | Goldie et al. |
| 5,149,543 A | 9/1992 | Cohen et al. |
| 5,188,837 A | 2/1993 | Domb |
| 5,266,331 A | 11/1993 | Oshlack et al. |
| 5,278,201 A | 1/1994 | Dunn et al. |
| 5,278,202 A | 1/1994 | Dunn et al. |
| 5,286,496 A | 2/1994 | Stapler et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,635 A | 10/1994 | Raman et al. |
| 5,382,424 A | 1/1995 | Stapler et al. |
| 5,391,381 A | 2/1995 | Wong et al. |
| 5,399,363 A | 3/1995 | Liversidge et al. |
| 5,478,577 A | 12/1995 | Sackler et al. |
| 5,487,898 A | 1/1996 | Lu et al. |
| 5,540,912 A | 7/1996 | Roorda et al. |
| 5,545,408 A | 8/1996 | Trigg et al. |
| 5,549,912 A | 8/1996 | Oshlack et al. |
| 5,569,450 A | 10/1996 | Duan et al. |
| 5,599,552 A | 2/1997 | Dunn et al. |
| 5,633,000 A | 5/1997 | Grossman et al. |
| 5,656,295 A | 8/1997 | Oshlack et al. |

(Continued)

FOREIGN PATENT DOCUMENTS

| | | |
|---|---|---|
| AU | 8374575 | 8/1975 |
| CA | 2222567 | 12/1996 |
| DE | 1569231 | 8/1969 |
| DE | 2213717 | 11/1972 |
| DE | 2321174 | 11/1973 |
| DE | 2438352 | 2/1976 |
| DE | 2720245 | 11/1977 |
| DE | 19714765 | 10/1998 |
| EP | 0244118 | 11/1987 |
| EP | 0290983 | 11/1988 |

(Continued)

OTHER PUBLICATIONS

Ahuja et al. Intra-Articular Morphine Versus Bupivacaine for Postoperative Analgesia Following Knee Arthroscopy (1996).*

(Continued)

*Primary Examiner* — David J Blanchard
*Assistant Examiner* — Sarah Alawadi

(57) ABSTRACT

The present invention relates to novel anesthetic compositions containing a non-polymeric carrier material and an anesthetic, where the compositions are suitable for providing a sustained local anesthesia without an initial burst and having a duration for about 24 hours or longer. Certain compositions are also provided that include a first anesthetic and a second anesthetic. In such compositions, the second anesthetic is a solvent for the first anesthetic and provides an initial anesthetic effect upon administration to a subject. The non-polymeric carrier may optionally be a high viscosity liquid carrier material such as a suitable sugar ester. The compositions can further include one or more additional ingredients including active and inactive materials. Methods of using the compositions of the invention to produce a sustained anesthetic effect at a site in a subject are also provided.

9 Claims, 6 Drawing Sheets

U.S. PATENT DOCUMENTS

| | | | |
|---|---|---|---|
| 5,672,360 | A | 9/1997 | Sackler et al. |
| 5,702,716 | A | 12/1997 | Dunn et al. |
| 5,725,841 | A | 3/1998 | Duan et al. |
| 5,728,396 | A | 3/1998 | Peery et al. |
| 5,733,950 | A | 3/1998 | Dunn et al. |
| 5,736,152 | A | 4/1998 | Dunn |
| 5,739,176 | A | 4/1998 | Dunn et al. |
| 5,747,051 | A | 5/1998 | Granger et al. |
| 5,747,058 | A * | 5/1998 | Tipton et al. .................. 424/423 |
| 5,750,100 | A | 5/1998 | Yamagata et al. |
| 5,759,563 | A | 6/1998 | Yewey et al. |
| 5,777,124 | A | 7/1998 | Zavareh et al. |
| 5,780,044 | A | 7/1998 | Yewey et al. |
| 5,786,484 | A | 7/1998 | Dyer et al. |
| 5,840,329 | A | 11/1998 | Bai |
| 5,879,705 | A | 3/1999 | Heafield et al. |
| 5,919,473 | A | 7/1999 | Elkhoury |
| 5,932,597 | A | 8/1999 | Brown |
| 5,942,241 | A | 8/1999 | Chasin et al. |
| 5,968,542 | A | 10/1999 | Tipton |
| 5,985,305 | A | 11/1999 | Peery et al. |
| 5,994,548 | A | 11/1999 | Langston et al. |
| 6,008,355 | A | 12/1999 | Huang et al. |
| 6,042,811 | A | 3/2000 | Duan et al. |
| 6,051,558 | A | 4/2000 | Burns et al. |
| 6,126,919 | A | 10/2000 | Stefely et al. |
| 6,143,322 | A | 11/2000 | Sackler et al. |
| 6,203,813 | B1 | 3/2001 | Gooberman |
| 6,245,351 | B1 | 6/2001 | Nara et al. |
| 6,291,013 | B1 | 9/2001 | Gibson et al. |
| 6,312,717 | B1 | 11/2001 | Molinoff et al. |
| 6,384,227 | B2 | 5/2002 | Dyer et al. |
| 6,403,609 | B1 | 6/2002 | Asgharian |
| 6,413,536 | B1 | 7/2002 | Gibson et al. |
| 6,426,339 | B1 | 7/2002 | Berde et al. |
| 6,440,493 | B1 | 8/2002 | Gibson et al. |
| 6,479,074 | B2 | 11/2002 | Murdock et al. |
| 6,486,138 | B1 | 11/2002 | Asgharian et al. |
| 6,498,153 | B1 | 12/2002 | Cady et al. |
| 6,514,516 | B1 | 2/2003 | Chasin et al. |
| 6,521,259 | B1 | 2/2003 | Chasin et al. |
| 6,524,607 | B1 | 2/2003 | Goldenheim et al. |
| 6,699,908 | B2 | 3/2004 | Sackler et al. |
| 6,733,783 | B2 | 5/2004 | Oshlack et al. |
| 6,921,541 | B2 | 7/2005 | Chasin et al. |
| 6,992,065 | B2 | 1/2006 | Okumu |
| 7,053,209 | B1 | 5/2006 | Gibson et al. |
| 7,833,543 | B2 | 11/2010 | Gibson et al. |
| 2001/0000522 | A1 | 4/2001 | Dyer et al. |
| 2001/0029257 | A1 | 10/2001 | Murdock et al. |
| 2002/0001631 | A1* | 1/2002 | Okumu .................. 424/641 |
| 2002/0114835 | A1 | 8/2002 | Sackler et al. |
| 2003/0045454 | A1 | 3/2003 | Okumu et al. |
| 2003/0152618 | A1* | 8/2003 | Chasin et al. .................. 424/501 |
| 2003/0185873 | A1 | 10/2003 | Chasin et al. |
| 2004/0001889 | A1 | 1/2004 | Chen et al. |
| 2004/0024021 | A1 | 2/2004 | Sudo et al. |
| 2004/0052336 | A1 | 3/2004 | Langlet et al. |
| 2004/0101557 | A1* | 5/2004 | Gibson et al. .................. 424/484 |
| 2004/0109893 | A1 | 6/2004 | Chen et al. |
| 2004/0138237 | A1 | 7/2004 | Shah |
| 2004/0146562 | A1 | 7/2004 | Shah |
| 2004/0224903 | A1 | 11/2004 | Berry et al. |
| 2005/0042194 | A1 | 2/2005 | Ng et al. |
| 2005/0106304 | A1 | 5/2005 | Cook et al. |
| 2005/0171052 | A1 | 8/2005 | Cook et al. |
| 2005/0232876 | A1 | 10/2005 | Minga et al. |
| 2005/0244489 | A1 | 11/2005 | Paris |
| 2005/0266087 | A1 | 12/2005 | Junnarkar et al. |
| 2006/0034926 | A1 | 2/2006 | Fraatz et al. |
| 2006/0058401 | A1 | 3/2006 | Ishikawa et al. |
| 2006/0165800 | A1 | 7/2006 | Chen et al. |
| 2006/0210599 | A1 | 9/2006 | Gibson et al. |
| 2008/0023261 | A1 | 1/2008 | Kaneko et al. |
| 2008/0145419 | A1 | 6/2008 | Gibson et al. |
| 2008/0152708 | A1 | 6/2008 | Gibson et al. |
| 2008/0206321 | A1 | 8/2008 | Yum et al. |
| 2009/0023689 | A1 | 1/2009 | Yum et al. |
| 2009/0023690 | A1 | 1/2009 | Yum et al. |
| 2009/0036490 | A1 | 2/2009 | Verity |
| 2011/0009451 | A1 | 1/2011 | Verity |

FOREIGN PATENT DOCUMENTS

| | | |
|---|---|---|
| EP | 0535899 | 4/1993 |
| EP | 0537559 | 4/1993 |
| EP | 0539559 | 5/1993 |
| EP | 0539751 | 5/1993 |
| EP | 0621042 | 10/1994 |
| EP | 0635531 | 1/1995 |
| EP | 0640336 | 3/1995 |
| EP | 0711548 | 5/1996 |
| EP | 0773034 | 5/1997 |
| EP | 00999825 | 5/2000 |
| EP | 1010436 | 6/2000 |
| EP | 0782569 | 3/2002 |
| EP | 0804417 | 6/2003 |
| EP | 0788480 | 7/2003 |
| EP | 0788481 | 8/2003 |
| EP | 1348427 | 10/2003 |
| EP | 1032390 | 11/2003 |
| EP | 0778768 | 5/2004 |
| EP | 1548093 | 6/2005 |
| EP | 2238478 | 10/2010 |
| GB | 1088992 | 10/1967 |
| GB | 2238478 | 6/1991 |
| JP | 59210024 | 11/1984 |
| JP | 62000419 | 1/1987 |
| JP | 2096516 | 4/1990 |
| JP | 5194273 | 8/1993 |
| JP | 7053356 | 2/1995 |
| JP | 7112940 | 5/1995 |
| JP | 7115901 | 5/1995 |
| JP | 7124196 | 5/1995 |
| JP | 9502181 | 3/1997 |
| WO | WO 9003768 | 4/1990 |
| WO | WO 9003809 | 4/1990 |
| WO | WO 9117900 | 11/1991 |
| WO | WO 9118016 | 11/1991 |
| WO | WO 9303751 | 3/1993 |
| WO | WO 9307833 | 4/1993 |
| WO | WO 94/05265 | 3/1994 |
| WO | WO 9415587 | 7/1994 |
| WO | WO 95/09613 | 4/1995 |
| WO | WO 9517901 | 7/1995 |
| WO | WO 96/09290 | 3/1996 |
| WO | WO 96/12699 | 5/1996 |
| WO | WO 96/12700 | 5/1996 |
| WO | WO 96/22281 | 7/1996 |
| WO | WO 96/41616 | 12/1996 |
| WO | WO 9639995 | 12/1996 |
| WO | WO 9715285 | 5/1997 |
| WO | WO 9727840 | 8/1997 |
| WO | WO 97/49391 | 12/1997 |
| WO | WO 9827962 | 7/1998 |
| WO | WO 9827963 | 7/1998 |
| WO | WO 9834596 | 8/1998 |
| WO | 9844903 | 10/1998 |
| WO | WO 98/51246 | 11/1998 |
| WO | WO 9853837 | 12/1998 |
| WO | WO 99/06023 | 2/1999 |
| WO | WO 9913913 | 3/1999 |
| WO | WO 99/25349 | 5/1999 |
| WO | WO 00/00120 | 1/2000 |
| WO | WO 0078335 | 12/2000 |
| WO | WO 0115734 | 3/2001 |
| WO | WO 01/51024 | 7/2001 |
| WO | WO 01/76599 | 10/2001 |
| WO | 0210436 | 2/2002 |
| WO | WO 02/053187 | 7/2002 |
| WO | WO 03/000282 | 1/2003 |
| WO | 03041684 | 5/2003 |
| WO | WO 03/086368 | 10/2003 |
| WO | WO 03/101358 | 12/2003 |
| WO | 2004011032 | 2/2004 |
| WO | WO 2004/037224 | 5/2004 |
| WO | WO 2004/037289 | 5/2004 |
| WO | WO 2004052336 | 6/2004 |

| | | |
|---|---|---|
| WO | WO 2004/056338 | 7/2004 |
| WO | WO 2004/082658 | 9/2004 |
| WO | WO 2004/101557 | 11/2004 |
| WO | WO 2005/009408 | 2/2005 |
| WO | WO 2005/048744 | 6/2005 |
| WO | WO 2005/105031 | 11/2005 |
| WO | WO 2005/115333 | 12/2005 |
| WO | WO 2006/084139 | 8/2006 |
| WO | WO 2006/084141 | 8/2006 |
| WO | WO 2008023261 | 2/2008 |

OTHER PUBLICATIONS

Johnson, R.M., et al. "Applications of Continuous Site-Directed Drug Delivery", Proc. West. Pharmacol. Soc. vol. 45: 219-222 (2002).

"New Drugs/Programs", Current Drug Discovery, Nov. 2004 pp. 7-10.

Sullivan, S. A., 1998, "Sustained Release of Orally Administered Active Using Saber™ Delivery System Incorporated Into Soft Gelatin Capsules," Proceed. Int'/. Symp. Control. ReJ. Bioael. Mater., 25:918-919.

"3M DDS Announces Development of New HFA-Compatible Excipients: Novel Oligomeric Acids as MDI Suspension Aids and Solubilizers," 3M Delivery Newsletter, 3M Drug Delivery Systems, vol. 15, Jun. 2000.

Adams EG, et al. "A comparison of the abuse liability of tramadol, NSAIDS, and hydrocodone in patients with chronic pain." Journal of Pain and Symptom Management. 3 1(5), 465-476 2006.

Ajayaghosh, A., et al., "Solid-Phase Synthesis of N-Methyl and N-Ethylamides of Peptides Using Photolytically Detachable ((3-Nitro-4-((alkylamino)methyl) benzamido)methyl)polystrene Resin," J. Org. Chem., 55:2826 (1990).

Allahham A, et at. "Flow and injection characteristics of pharmaceutical parenteral formulations using a micro-capillary rheometer". Int J Pharm. 2004;270(1-2): 139-48.

Ansel, H.C. et al., Pharmaceutical Dosage Forms and Drug Delivery System, sixth ed., (1995).

Barb, R. et al., "Evaluation of the Saber Delivery System for the Controlled Release of Deslorelin: Effect of Dose in Estrogen Primed Ovarectomized Gilts," Proceed. Int'l Symp. Control. Rel. Bioact. Mater., 26 (1999).

Becker, S.E., et al. "Effects of Gonadotropin-Releasing Hormone Infused in a Pulsatile or Continuous Fashion on Serum Gonadotropin Concentrations and Ovulation in the Mare," J. Anim. Sci. (1992) 70:1208-1215.

Bekersky I, et al. "Effect of low- and high-fat meals on tacrolimus absorption following 5 mg single oral doses to healthy human subjects." J Clin Pharmacol 2001 ; 4 1 (2): 176-82.

Betschart, R., et al., "Evaluation of the Saber™ Delivery System for the Controlled Release of the GnRH Analogue Deslorelin for Advancing Ovulation in Mares: Effect of Gamma Radiation," Proceed. Int'l Symp. Control. Rel. Bioact. Mater. 25 (1998) Controlled Release Society, Inc. pp. 655-656.

Brevard J, et al. "Pain and opioid abuse in a population of substance abuse patients: data from the NAVIPPRO system." Conference paper presented at the 42nd American Pain Society (APS) Annual Scientific Meeting, Washington D.C., 2007.

Buhler, K. GnRH Agonists and Safety, In GnRH Analogues The State of the Art 1993, A Summary of the 3rd International Symposium on GnRH Analogues in Cancer and Human Reproduction, Geneva, Feb. 1993.

Burns, P. et al., "Pharmacodynamic Evaluation of the Saber.™. Delivery System for the Controlled Release of the GnRH Analogue Deslorelin Acetate for Advancing Ovulation in Cyclic Mares," Proceed. Int'l. Symp. Control. Rel. Bioact. Mater., 24 (1997), Controlled Release Society, Inc.

Cellulose Acetate Butyrate. In: European pharmacopoeia. 4 edn. Strasbourg Cedex, France: Council of Europe; 200 1 ; p. 853-4.

Coy, et al., "Solid Phase Synthesis of Lutcinizing Hormone-Releasing Hormone and Its Analogs," Methods Enzymol. 37, 416 (1975).

Desai, Neil P., et al. "Surface Modifications of Polymeric Biomaterials for Reduced Thrombogenicity," Polymeric Materials Science and Engineering, vol. 62, 1990 by ACS.

Dodson, K.M., Et al. "Oral Controlled Release of Antiretrovirals Using the SABER Delivery System Incorporated into Soft Gelatin Capsules", AAPS Meeting, 1999, New Orleans, LA.

Duan, D. et al., "Novel Dispersing Aids for Hydrofluoroalkane-Based Metered Dose Inhalers," 1998 Conference of the American Association of Pharmaceutical Scientists, San Francisco, California, Nov. 1998.

Duan, D. et al., "Oligomeric Lactic Acids as Solubilizing Aids for HFA-Based Metered Dose Inhalers," 1998 Conference of the American Association of Pharmaceutical Scientists, San Francisco, California, Nov. 1998.

Dunbar SA, Katz NP "Chronic opioid therapy for nonmalignant pain in patients with a history of substance abuse: report of 20 cases." Journal of Pain and Symptom Management. 1 1 (3), 163-171. 1996.

Fitzgerald, B.P, et al., "Effect of Constant Administration of a Gonadotropin-Releasing Hormone Agonist on Reproductive Activity in Mares: Preliminary Evidence on Suppression of Ovulation During the Breeding Season," Am. J. Vet. Res., 54:10 1746-1751, Oct. 1993.

Fleury, J., et al., "Evaluation of the Saber.™. Delivery System for the Controlled Release of the Deslorelin for Advancing Ovulation in the Mare: Effects of Formulation & Dose," Proceed. Int'l. Symp. Control. Rel. Bioact. Mater. 25 (1998) Controlled Release Society, Inc. pp. 657-658.

Gilderman L., et al. "Remoxy™: A New Opioid Drug With Effective Analgesia and Abuse-Resistance." American Pain Society Annual Meeting, San Antonio, TX, May 2006.

Ginther, O.J. et al. "Effect of a Synthetic Gonadotropin-Releasing Hormone on Plasma Concentrations of Luteinizing Hormone in Ponies," Am. J. Vet. Res., 35: 79-81 (1974).

Ginther, O.J., "Ultrasonic Imaging and Reproductive Events in the Mare," Equiservices, Cross Plains, WI Chapter 4:43-72 (1986).

Ginther, O.J., Reproductive Biology of the Mare: Basic and Applied Aspects, EquiServices, Chapter 12, 499-508 Cross Plains, Wisconsin (1970).

Glajchen, M. "Chronic Pain: Treatment Barriers and Strategies for Clinical Practice." J Am Board Fam Pract. 2001 ; 14(3): 178-183.

Harrison, L., et al. "Comparison of HCG, Buserelin and Luprostiol for Induction of Ovulation in Cyclling Mares," J. Eq. Vet. Sci., 11:163-166 (1991).

Hatakeyama et al., "Synthesis and physical properties of polyurethanes from saccharide-based polycaprolactones." Macromolecular Symposia, vol. 130, pp. 127-138, 1998.

Hays LR. "A profile of OxyContin addiction. Journal of Addictive Diseases." 23 (4), 1-9. 2004.

Henry, C. "Surcrose Acetate Isobutyrate Special Grade for Beverage Applications", 1995.

Hoskin PJ, et al. "The bioavailability and pharmacokinetics of morphine after intravenous, oral and buccal administration in healthy volunteers." Br J Clin Pharmacol 1989; 27 (4):499-505.

Hyland, J.H., et al. "Infusion of Gonadotrophin-Releasing Hormone (GnRH) Induces of Ovulation and Fertile Oestrus in Mares During Seasonal Anoestrus," J. Reprod. Fert., Suppl. 35 (1987), 211-220.

Inciardi JA, Surratt HL, Kurtz SP, Cicero TJ. "Mechanisms of prescription drug diversion amoung drug-involved club- and street-based populations." Pain Medicine. 8(2), 171-183, Mar. 2007.

Irvine, C.H.G., "GnRH Clinical Application," In Equine Reproduction, (eds) McKinon, A.O. and Voss, J.L., Chapter 36, pp. 41-45, Lea & Febiger (1993).

Irvine, D.S., "Duration of Oestrus and Time of Ovulation in Mares Treated with Synthetic GnRH (Ay24,031)," J. Reprod. Fert. Supp. 23:279-283 (1975).

Ishida T, Oguri K, et al. "Isolation and identitication of urinary metabolites of oxycodone in rabbits." Drug Metab Dispos 1979; 7 (3): 162-5.

Ishida T, Oguri K, Yoshimura H. "Determination of oxycodone metabolites in urines and feces of several mammalian species." J Pharmacobiodyn 1982; 5 (7):52 1-5.

Iyakuhin Tenkabutsu Kenkyykai Ed. "Jitsuyo Iyakuhin Tenkabutsu (Practical Medical Additives)" pub. Kagaku Kogyo-sha Mar. 5, 1974, Tokyo.

Jochle, W., et al., Control of Ovulation in the Mare with Ovuplant.™., a Short-Term Release Implant (STI) Containing the GNRH Analogue Deslorelin Acetate: J. Eq. Vet. Sci., 44:632 (1994).

Johnston LD, O'Malley PM, Bachman JG, Schulenberg, JE. "Monitoring the future. National results on adolescent drug use: overview of key findings" (NIH Publication No. 05-5726). Bethesda. MD: National Institute on Drug Abuse 2004.

Katz NP, et al. "Behavioral monitoring and urine toxicology testing in patients receiving long-term opioid therapy." Anesth Analg. 97(4), 1097-102.2003.

Katz NP, et al. "Challenges in the development of prescription opioid abuse-deterrent formulations." Clin J Pain. 2007;23(8):648-60.

Katz NP, et al. "Development and preliminary experience with an ease of extractability rating system for prescription opioids." Drug Development and Industrial Pharmacy. 32(6) 727-746(20). 2006.

Katz NP, et al. "Prescription monitoring of medical and non-medical Schedule II opioid abuse in Massachusetts: 1996-2005." Conference paper presented at the 69th College on Problems of Drug Dependence (CPDD). Quebec, Canada, 2007.

Kulkarni et al., "Polyactic Acid for Surgical Implants," Arch. Surg., 93:389 (1966).

Lacoste, D., et al., "Reversible Inhibition of Testicular Androgen Secretion by 3-, 5- and 6-Month Controlled-Release Microsphere Formulations of teh LH-RH Agonist [D-Trp.sup.6, des-Gly-NH.sub.2.sup.10] LH-RH Ethylamide in the Dog," J. Steroid Biochem. 33:5, 1007-1011, 1989.

Lalovic B, et al. "Pharmacokinetics and pharmacodynamics of oral oxycodone in healthy human subjects: role of circulating active metabolites" Clin Pharmacol Ther 2006; 79 (5):461-79.

Loy, R.G. et al. "The Effects of Human Chorionic Gonadotrophin on Ovulation, Length of Estrus, and Fertility in the Mare," Cornell Vet. 56:41-50 (1966).

Material Safety Data Sheet of Eastman Chemical Products, "SAIB" Sucrose Acetate Isobutyrate, pp. 2-18, submitted May 10, 2011.

Material Safety Data Sheet of Eastman Fine Chemical Pharmaceutical Ingredients, Sucrose Acetate Isobutyrate Special Grade (SAIB-SG), Publication No. EFC-211, (May 1991).

Material Safety Data Sheet of Eastman Products for the Food Industry, "Sucrose Acetate Isobutyrate (SAIB-SB) for Use in Fruit-Flavored Beverages," Publication No. ZM-90, pp. 2-7 (Sep. 1989).

McCabe et al. "Motives, diversion and routes of administration associated with nonmedical use of prescription opioids." Addictive Behaviors. 32, 562-575. 2007.

McCarthy, P. et al., "Management of Stallions on Large Breeding Farms," Stallion Management, vol. 8, No. 1, Apr. 1992, pp. 219-235.

McKinnon, A.O., et al. "Effect of a GnRH Analogue (Ovuplant), hCG and Dexamethasone on Time to Ovulation in Cycling Mares." World Equine Veterinary Review, (1997) 2:3 16-18.

McKinnon, A.O., et al. "Repeated Use of a GnRH Analogue Deslorelin (Ovuplant) for Hastening Ovulation in the Transitional Mare," Equine Vet. J., (1996) 29:2 153-155.

McLellan AT, Luborsky L, Woody GE, O'Brien CP. "An improved 'diagnostic instrument for substance abuse patients." The Addiction Severity Index. J Nerv Ment Dis. 1980; 168:26-33.

Mearns, "Changing Seasons," The Blood-Horse, Sep. 28, 1996, p. 4794-4795.

Merrifield, B., "Solid Phase Synthesis" Science 232:342 (1986).

Meyer RJ, et al. Awareness topic: mitigating the risk of ethanol induced dose dumping from oral sustained controlled release dosage forms. In: FDA's Advisory Committee for Pharmaceutical Science Meeting. Oct. 2005.

Montovan, S.M., et al., "The Effect of a Potent GnRH Agonist on Gonadal and Sexual Activity in the Horse," Theriogenology, 33:6, 1305-1321 (1990).

Mumford, E.L. et al., "Use of Deslorelin Short-Term Implants to Induce Ovulation in Cycling Mares During Three Consecutive Estrov Cycles," Animal Reproduction Science, 139 (1995) 129-140.

Murray S, et al. "Alcohol-associated rapid release of a long-acting opioid" CMAJ 2005; 173(7):756.

Nakagaki "Seizai Butsuri Kagaku (Physical Chemistry of Medical Preparations)", pub. Asakura Shoten, Nov. 5, 1968, Tokyo.

Nally, J., et al., "Induction of Mucosal IgA Specific for SeMF3 for *Streptococcus equi* with Intranasal Vaccination Using a Sucrose Acetate Isobutyrate Based Delivery System", Proceed. Int'l. Symp. Control. Rel. Bioact. Mater., 26 (1999) Controlled Release Society, Inc.

Nett et al., "Further Studies on the Radioimmunoassay of Gonadotropin-Releasing Hormone: Effect of Radioiodination, Antiserum and Unextracted Serum on Levels of Immunoreactivity in Serum," Endocrinology 101:1135 (1977).

Pulido et al., "Enzymatic Regioselective Acylation of Hexoses and Pentoses Using Oxime Esters.", J. Chem. Soc. Perkin Trans. 1, (21), 2891-2898, 1992.

Rabb et al., "Effects of Active Immunisation Against GnRH on LH, FSH and Prolactin Storage, Sectretion and Response to Their Secretagogues in Pony Geldings," J. Anim. Sci., 68:3322-3329 (1990).

Reynolds, R.C. et al., "Sucrose acetate isobutyrate (SAIB): historical aspects of its use in beverages and a review of toxicity studies prior to 1988," Food Chem. Toxicol., 1998,36 (2), pp. 81-93.

Reynolds, R.C., "Metabolism and pharmacokinetics of sucrose acetate isobutyrate (SAIB) and sucrose octaisobutyrate (SOIB) in rats, dogs, monkeys or humans: a review," Food Chem. Toxicol. . 1998.36 (2). pp. 95-99.

Roser, J.J., et al., "The Development of Antibodies to Human Chorionic Gonadotrpins Following its Repeated Injection in the Cyclic Mare," J. Reprod. Fert. Suppl., 173-179 (1979).

Sullivan, J., "Duration of Estrus and Ovulation Time in Nonlactating Mares Given Human Chorionic Gonadotropin During Three Successive Estrous Periods," J. Am. Vet. Med. Assoc., 63:895 (1973).

Swiderski et al., "Application of 14C Isotope in Studies on the Lability of Sugar Substituents" Nukleonika, Supl., vol. 10, pp. 347-352, 1966.

Thompson, Jr., D.L., et al., "Effects of Melatonin and Thyrotropin Releasing Hormone of Mares Durign the Nonbreeding Season," J. Anim. Sci., 58:3, 668-677(1983).

Thompson, Jr., D.L., et al., "Testosterone Effects on Mares During Synchronization with Altrenogest: FSH, LH, Estrous, Duration and Pregnancy Rate" J. Anim. Sci., 56:3, 678-686 (1983).

Trescot AM, et al. "Opioid Guidelines in the Management of Chronic Non-Cancer Pain." Pain Physician. 2006;9: 1-40.

Vega-Rios A, Villalobos H, Mata-Segreda JF. "Acid-catalyzed hydrolysis of triacylglycerols obeys monoexponential kinetics." Int J Chem Kinet. 1992; 24:887-94.

Voss, J.L. et al. "The Effect of HCG on Duration of Oestrus, Ovulation Time and Fertility in Mares," J. Reprod. Fert., Suppl. 23 (1975) 297-301.

Japanese Office Action for Japanese Patent Application No. 2007-532447 mailed Nov. 15, 2011.

* cited by examiner

CONTROLLED DELIVERY SYSTEM

This application is a continuation of co-pending U.S. application Ser. No. 11/663,125, filed on Aug. 29, 2008, which is a Section 371 U.S. national stage filing of International application No. PCT/US05/032863, filed on Sep. 15, 2005, which claims benefit of U.S. Provisional application Ser. No. 60/610,797, filed on Sep. 17, 2004 and U.S. Provisional application Ser. No. 60/691,395, filed on Jun. 17, 2005.

TECHNICAL FIELD

The present invention relates generally to the field of controlled delivery systems, and more particularly controlled delivery systems containing an active agent that is able to provide a localized anesthetic effect, where the systems are suitable for use in connection with surgical and medical treatments, and as medicaments for use in post operative recovery procedures.

BACKGROUND OF THE INVENTION

Biodegradable controlled delivery systems for active agents are well known in the art. Biodegradable carriers for drug delivery are useful because they obviate the need to remove the drug-depleted device.

The most common carrier materials used for controlled delivery systems are polymers. The field of biodegradable polymers has developed rapidly since the synthesis and biodegradability of polylactic acid was reported by Kulkarni et al. (1966) Arch. Surg. 93:839. Examples of other polymers which have been reported as useful as a matrix material for controlled delivery systems include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, e.g., U.S. Pat. Nos. 4,891,225 and 4,906,474 (polyanhydrides); U.S. Pat. No. 4,767,628 (polylactide, polylactide-co-glycolide acid); U.S. Pat. No. 4,530,840 (polylactide, polyglycolide, and copolymers); and U.S. Pat. No. 5,234,520 (biodegradable polymers for controlled delivery in treating periodontal disease).

Degradable materials of biological origin are well known including, for example, crosslinked gelatin. Hyaluronic acid has been crosslinked and used as a degradable swelling polymer for biomedical applications (see, e.g., U.S. Pat. No. 4,957,744 and Della Valle et al. (1991) Polym. Mater. Sci. Eng., 62:731-735).

Biodegradable hydrogels have also been developed for use in controlled delivery systems and serve as carriers of biologically active materials such as hormones, enzymes, antibiotics, antineoplastic agents, and cell suspensions. See, e.g., U.S. Pat. No. 5,149,543.

Hydrogel compositions are also commonly used as substrates for cell and tissue culture, impression materials for prosthetics, wound-packing materials, or as solid phase materials in size exclusion or affinity chromatography applications. For example, nonporous, deformed and/or derivatized agarose hydrogel compositions have been used in high-performance liquid chromatography and affinity chromatography methods (Li et al. (1990) Preparative Biochem. 20:107-121), and superporous agarose hydrogel beads have been used as a support in hydrophobic interaction chromatography (Gustavsson et al. (1999) J. Chromatography 830:275-284).

Many dispersion systems are also currently in use as carriers of substances, particularly biologically active compounds. Dispersion systems used for pharmaceutical and cosmetic formulations can be categorized as either suspensions or emulsions. Suspensions are comprised of solid particles ranging in size from a few nanometers up to hundreds of microns, dispersed in a liquid medium using suspending agents. Solid particles include microspheres, microcapsules, and nanospheres. Emulsions are generally dispersions of one liquid in another stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, for example, those described in U.S. Pat. Nos. 4,622,219 and 4,725,442. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

A number of systems for forming an implant in situ have been described. For example, U.S. Pat. No. 4,938,763 describes a method for forming an implant by dissolving a non-reactive, water insoluble thermoplastic polymer in a biocompatible, water-soluble solvent to form a liquid, placing the liquid within the body, and allowing the solvent to dissipate to produce a solid implant. The polymer solution can be placed in the body via syringe. The implant can assume the shape of its surrounding cavity. Alternatively, an implant can be formed from reactive, liquid oligomeric polymers which contain no solvent and which cure in place to form solids, usually with the addition of a curing catalyst.

A number of polymeric controlled delivery systems for the delivery of local anesthetics have been described in the art. Although such polymeric delivery systems may provide suitable controlled release properties for the anesthetic and further overcome disadvantages associated with injection of neat anesthetics (e.g., dispersion away from the target site, entry into blood stream, and systemic toxicities), it is difficult to overcome certain disadvantages associated with the polymeric systems, such as failure to avoid systemic initial burst release of the anesthetic or having to provide enhancer agents in order to overcome too little release of the anesthetic from the systems.

SUMMARY OF THE INVENTION

Non-polymeric controlled delivery carrier systems for administration of an anesthetic agent of interest are provided. It is thus an object of the present invention to provide a long-acting controlled delivery system that releases an anesthetic over a prolonged period of time, sufficient to provide a local anesthetic effect at a site of administration for at least about 24 hours after administration, preferably at least about 36 to 48 hours after administration, and more preferably at least about 48 to 72 hours after administration. It is also an object of the present invention that release of the active anesthetic agent from the long-acting anesthetic composition occurs without an initial burst.

It is more particularly an object of the present invention to provide a composition containing an anesthetic and a pharmaceutically acceptable non-polymeric carrier. The non-polymeric carrier controls release of the anesthetic to provide an anesthetic effect characterized by sustained local anesthesia after administration to a subject without an initial burst and a duration of at least about 24 hours after administration, preferably at least about 36 to 48 hours after administration, and more preferably at least about 48 to 72 hours after administration.

In one aspect of the invention, the non-polymeric carrier is sufficient to provide either a first order controlled release profile of the anesthetic, or a pseudo-zero order release profile of the anesthetic. In certain embodiments, the anesthetic is a local anesthetic, for example an amide- or ester-type local anesthetic. In a preferred embodiment, the anesthetic is bupivacaine that may further be provided in free base form. In other embodiments, the composition is capable of providing a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL.

In another aspect of the invention, the non-polymeric carrier is substantially insoluble in water or in an aqueous biological system. In such compositions, the pharmaceutical may further contain a solvent that is dispersible, soluble or miscible in water or in an aqueous system. The solvent may thus be an organic solvent that is capable of dissipating, diffusing or leaching away from the composition upon placement within a biological system, whereby the carrier can then coagulate or precipitate to form a solid implant in situ.

In yet another aspect of the invention, the non-polymeric carrier is a liquid, preferably a high viscosity liquid carrier material ("HVLCM") having a viscosity of at least about 5,000 cP at 37° C. and which does not crystallize neat under ambient or physiological conditions. Such liquid carrier materials can be combined with a solvent in which the carrier material is soluble. If a HVLCM is used, it is preferred that the solvent is sufficient to lower the viscosity of the HVLCM. In certain embodiments, the solvent may be a second anesthetic agent such as benzyl alcohol. The compositions may be provided in any suitable form, for example, as an emulsion, a paste, a gel, a slurry, a cream, a film, a spray, a solid, a particle, a microparticle, a powder, an implant, or a liquid. In certain embodiments, the composition further includes a material that is immiscible with the non-polymeric carrier, for example where the composition is an emulsion. In these compositions, the carrier may be present in either the dispersed or the continuous phase of the emulsion.

It is also an object of the present invention to provide a composition containing an anesthetic and a pharmaceutically acceptable non-polymeric carrier. The non-polymeric carrier controls release of the anesthetic to provide an anesthetic effect characterized by sustained local anesthesia after administration to a subject, where the composition is further capable of providing a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL.

In one aspect of the invention, the composition is capable of providing a sustained mean steady state plasma concentration ($C_{ss}$) for a period of at least about 48 hours. In another aspect, the composition is further characterized as not having any substantial initial burst. In still other aspects, the non-polymeric carrier is sufficient to provide either a first order controlled release profile of the anesthetic, or a pseudo-zero order release profile of the anesthetic. In certain embodiments, the anesthetic is a local anesthetic, for example an amide- or ester-type local anesthetic. In a preferred embodiment, the anesthetic is bupivacaine that may further be provided in free base form.

In another aspect of the invention, the non-polymeric carrier is substantially insoluble in water or in an aqueous biological system. In such compositions, the pharmaceutical may further contain a solvent that is dispersible, soluble or miscible in water or in an aqueous system. The solvent may thus be an organic solvent that is capable of dissipating, diffusing or leaching away from the composition upon placement within a biological system, whereby the carrier can then coagulate or precipitate to form a solid implant in situ.

In yet another aspect of the invention, the non-polymeric carrier is a liquid, preferably a high viscosity liquid carrier material ("HVLCM") having a viscosity of at least about 5,000 cP at 37° C. and which does not crystallize neat under ambient or physiological conditions. Such liquid carrier materials can be combined with a solvent in which the carrier material is soluble. If a HVLCM is used, it is preferred that the solvent is sufficient to lower the viscosity of the HVLCM. In certain embodiments, the solvent may be a second anesthetic agent such as benzyl alcohol. The compositions may be provided in any suitable form, for example, as an emulsion, a paste, a gel, a slurry, a cream, a film, a spray, a solid, a particle, a microparticle, a powder, an implant, or a liquid. In certain embodiments, the composition further includes a material that is immiscible with the non-polymeric carrier, for example where the composition is an emulsion. In these compositions, the carrier may be present in either the dispersed or the continuous phase of the emulsion.

It is a related object of the invention to provide a composition containing a first anesthetic, a second anesthetic, and a pharmaceutically acceptable non-polymeric carrier. In the composition, the second anesthetic is a solvent for the first anesthetic and provides an initial anesthetic effect upon administration to a subject. The non-polymeric carrier controls release of the first anesthetic to provide a subsequent anesthetic effect characterized by sustained local anesthesia having an onset within about 2 hours of administration to a subject without an initial burst and a duration of at least about 24 hours after administration, preferably at least about 36 to 48 hours after administration, and more preferably at least about 48 to 72 hours after administration.

In one aspect of the invention, the non-polymeric carrier is sufficient to provide either a first order controlled release profile of the anesthetic, or a pseudo-zero order release profile of the anesthetic. In other embodiments, the composition is capable of providing a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL. In certain other embodiments, the first anesthetic is a local anesthetic, for example an amide- or ester-type local anesthetic. In still further embodiments, the second anesthetic is also a solvent for the non-polymeric carrier. The second anesthetic may be an alcohol, aromatic alcohol, acid or acid derivative solvent, or any combination of such solvents. In a preferred embodiment, the second anesthetic is benzyl alcohol. In another preferred embodiment, the first anesthetic is bupivacaine that may further be provided in free base form.

In another aspect of the invention, the non-polymeric carrier is substantially insoluble in water or in an aqueous biological system. In such compositions, the pharmaceutical may further contain a solvent that is dispersible, soluble or miscible in water or in an aqueous system. The solvent may thus be an organic solvent that is capable of dissipating, diffusing or leaching away from the composition upon placement within a biological system, whereby the carrier can then coagulate or precipitate to form a solid implant in situ.

In yet another aspect of the invention, the non-polymeric carrier is a liquid, preferably a high viscosity liquid carrier material ("HVLCM") having a viscosity of at least about 5,000 cP at 37° C. and which does not crystallize neat under ambient or physiological conditions. Such liquid carrier materials can be combined with a solvent in which the carrier material is soluble. If a HVLCM is used, it is preferred that the solvent is sufficient to lower the viscosity of the HVLCM. In certain embodiments, the solvent may be a second anesthetic agent such as benzyl alcohol. The compositions may be provided in any suitable form, for example, as an emulsion, a paste, a gel, a slurry, a cream, a film, a spray, a solid, a particle, a microparticle, a powder, an implant, or a liquid. In certain embodiments, the composition further includes a material that is immiscible with the non-polymeric carrier, for example where the composition is an emulsion. In these compositions, the carrier may be present in either the dispersed or the continuous phase of the emulsion.

It is also a related object of the invention to provide a composition comprising a non-polymeric, non-water soluble high viscosity liquid carrier material ("HVLCM") having a viscosity of at least 5,000 cP at 37° C. that does not crystallize neat under ambient or physiological conditions, a first anesthetic and a second anesthetic. Here again the second anesthetic is a solvent for the first anesthetic and provides an initial anesthetic effect upon administration to a subject. The HVLCM controls release of the first anesthetic to provide a subsequent anesthetic effect characterized by sustained local anesthesia having an onset within about 2 hours of administration to a subject without an initial burst and a duration of at least about 24 hours after administration, preferably at least about 36 to 48 hours after administration, and more preferably at least about 48 to 72 hours after administration. In certain embodiments, the composition is capable of providing a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL.

In one aspect of the invention, the first anesthetic is a local anesthetic, for example an amide- or ester-type local anesthetic. In other embodiments, the second anesthetic is also a solvent for the HVLCM. The second anesthetic may be an alcohol, aromatic alcohol, acid or acid derivative solvent, or any combination of such solvents. In a preferred embodiment, the second anesthetic is benzyl alcohol. In another preferred embodiment, the first anesthetic is bupivacaine that may further be provided in free base form. In still other preferred embodiments, the HVLCM is an ester, such as a sugar ester like sucrose acetate isobutyrate. In these compositions, it may be useful to provide a solvent in which the HVVLCM is soluble.

It is further related object of the invention to provide a composition comprising a non-polymeric, non-water soluble high viscosity liquid carrier material ("HVLCM") having a viscosity of at least 5,000 cP at 37° C. that does not crystallize neat under ambient or physiological conditions, a first anesthetic and a second anesthetic. Here again the second anesthetic is a solvent for the first anesthetic and provides an initial anesthetic effect upon administration to a subject. The HVLCM controls release of the first anesthetic to provide a subsequent anesthetic effect characterized by sustained local anesthesia, where the composition is further capable of providing a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL.

In one aspect of the invention, the composition is capable of providing a sustained mean steady state plasma concentration ($C_{ss}$) for a period of at least about 48 hours. In another aspect, the composition is further characterized as not having any substantial initial burst.

In another aspect of the invention, the first anesthetic is a local anesthetic, for example an amide- or ester-type local anesthetic. In other embodiments, the second anesthetic is also a solvent for the HVLCM. The second anesthetic may be an alcohol, aromatic alcohol, acid or acid derivative solvent, or any combination of such solvents. In a preferred embodiment, the second anesthetic is benzyl alcohol. In another preferred embodiment, the first anesthetic is bupivacaine that may further be provided in free base form. In still other preferred embodiments, the HVLCM is an ester, such as a sugar ester like sucrose acetate isobutyrate. In these compositions, it may be useful to provide a solvent in which the HVVLCM is soluble.

It is a further object of the invention to provide a method for providing an anesthetic effect at a site in a subject. The method comprises administering a composition at, near, in, or adjacent to the site, where the composition includes an anesthetic and a pharmaceutically acceptable non-polymeric carrier. The non-polymeric carrier controls release of the anesthetic to provide an anesthetic effect characterized by sustained local anesthesia after administration to the subject without an initial burst and having a duration of at least about 24 hours after administration.

In one aspect of the invention, the anesthetic is a local anesthetic, for example an amide- or ester-type local anesthetic.

It is a related object of the invention to provide a method for providing an anesthetic effect at a site in a subject. The method comprises administering a composition at, near, in, or adjacent to the site, where the composition includes an anesthetic and a pharmaceutically acceptable non-polymeric carrier. The non-polymeric carrier controls release of the anesthetic to provide an anesthetic effect characterized by sustained local anesthesia after administration to the subject, where the composition is further capable of providing a sustained mean steady state plasma concentration ($C_{ss}$) of the anesthetic of at least about 200 ng/mL for a period of at least about 24 hours when the composition is administered subcutaneously.

In one aspect of the invention, the anesthetic is a local anesthetic, for example an amide- or ester-type local anesthetic.

It is a still further object of the invention to provide a method for providing an anesthetic effect at a site in a subject. The method comprises administering a composition at, near, in, or adjacent to the site, where the composition includes a first anesthetic, a second anesthetic, and a pharmaceutically acceptable non-polymeric carrier. The second anesthetic is a solvent for the first anesthetic and provides an initial anesthetic effect at the site upon administration. The non-polymeric carrier controls release of the first anesthetic to provide a subsequent anesthetic effect characterized by sustained local anesthesia at the site having an onset within about 2 hours of administration without an initial burst and a duration of at least about 24 hours after administration, preferably at least about 36 to 48 hours after administration, and more preferably at least about 48 to 72 hours after administration.

In one aspect of the invention, the non-polymeric carrier is a liquid, preferably a high viscosity liquid carrier material ("HVLCM") that is non-water soluble and has a viscosity of at least about 5,000 cP at 37° C. and further which does not crystallize neat under ambient or physiological conditions. Such liquid carrier materials can be combined with a solvent in which the carrier material is soluble. If a HVLCM is used, it is preferred that the solvent is sufficient to lower the viscosity of the HVLCM. In certain embodiments, the solvent may be a second anesthetic agent such as benzyl alcohol.

In another aspect of the invention, the first anesthetic is a local anesthetic, for example an amide- or ester-type local anesthetic. In other embodiments, the second anesthetic is also a solvent for the HVLCM. The second anesthetic may be an alcohol, aromatic alcohol, acid or acid derivative solvent, or any combination of such solvents. In a preferred embodiment, the second anesthetic is benzyl alcohol. In another preferred embodiment, the first anesthetic is bupivacaine that may further be provided in free base form. In still other preferred embodiments, the HVLCM is an ester, such as a sugar ester like sucrose acetate isobutyrate. In these compositions, it may be useful to provide a solvent in which the HVVLCM is soluble.

In yet another aspect of the invention, the composition is administered by topical administration, transdermal administration, injection or as an implant to the site. In certain embodiments, the composition is administered to a site that is a surgical wound, and the composition is administered into and/or adjacent to the wound.

It is a still further object of the invention to provide a method for providing an anesthetic effect at a site in a subject. The method comprises administering a composition at, near, in, or adjacent to the site, where the composition includes a first anesthetic, a second anesthetic, and a pharmaceutically acceptable non-polymeric carrier. The second anesthetic is a solvent for the first anesthetic and provides an initial anesthetic effect at the site upon administration. The non-polymeric carrier controls release of the first anesthetic to provide a subsequent anesthetic effect characterized by sustained local anesthesia at the site, and the composition is further capable of providing a sustained mean steady state plasma concentration ($C_{ss}$) of the anesthetic of at least about 200 ng/mL for a period of at least about 24 hours when the composition is administered subcutaneously.

In one aspect of the invention, the non-polymeric carrier is a liquid, preferably a high viscosity liquid carrier material ("HVLCM") that is non-water soluble and has a viscosity of at least about 5,000 cP at 37° C. and further which does not crystallize neat under ambient or physiological conditions. Such liquid carrier materials can be combined with a solvent in which the carrier material is soluble. If a HVLCM is used, it is preferred that the solvent is sufficient to lower the viscosity of the HVLCM. In certain embodiments, the solvent may be a second anesthetic agent such as benzyl alcohol.

In another aspect of the invention, the first anesthetic is a local anesthetic, for example an amide- or ester-type local anesthetic. In other embodiments, the second anesthetic is also a solvent for the HVLCM. The second anesthetic may be an alcohol, aromatic alcohol, acid or acid derivative solvent, or any combination of such solvents. In a preferred embodiment, the second anesthetic is benzyl alcohol. In another preferred embodiment, the first anesthetic is bupivacaine that may further be provided in free base form. In still other preferred embodiments, the HVLCM is an ester, such as a sugar ester like sucrose acetate isobutyrate. In these compositions, it may be useful to provide a solvent in which the HVVLCM is soluble.

In yet another aspect of the invention, the composition is administered by topical administration, transdermal administration, injection or as an implant to the site. In certain embodiments, the composition is administered to a site that is a surgical wound, and the composition is administered into and/or adjacent to the wound.

It is an advantage of the present invention that the non-polymeric carrier material is able to control release of the anesthetic agent to both avoid an initial burst release and to provide for a sustained anesthetic effect for at least about 24 hours. It is a further advantage of the invention that the compositions are readily constructed to provide any number of different pharmaceutical forms, and further to provide a wide range of different pharmacological release characteristics depending upon the intended site of administration and medical application.

These and other objects, aspects and advantages of the present invention will readily occur to the skilled practitioner upon reading the instant disclosure and specification.

DETAILED DESCRIPTION OF SPECIFIC EMBODIMENTS

Figure 1:
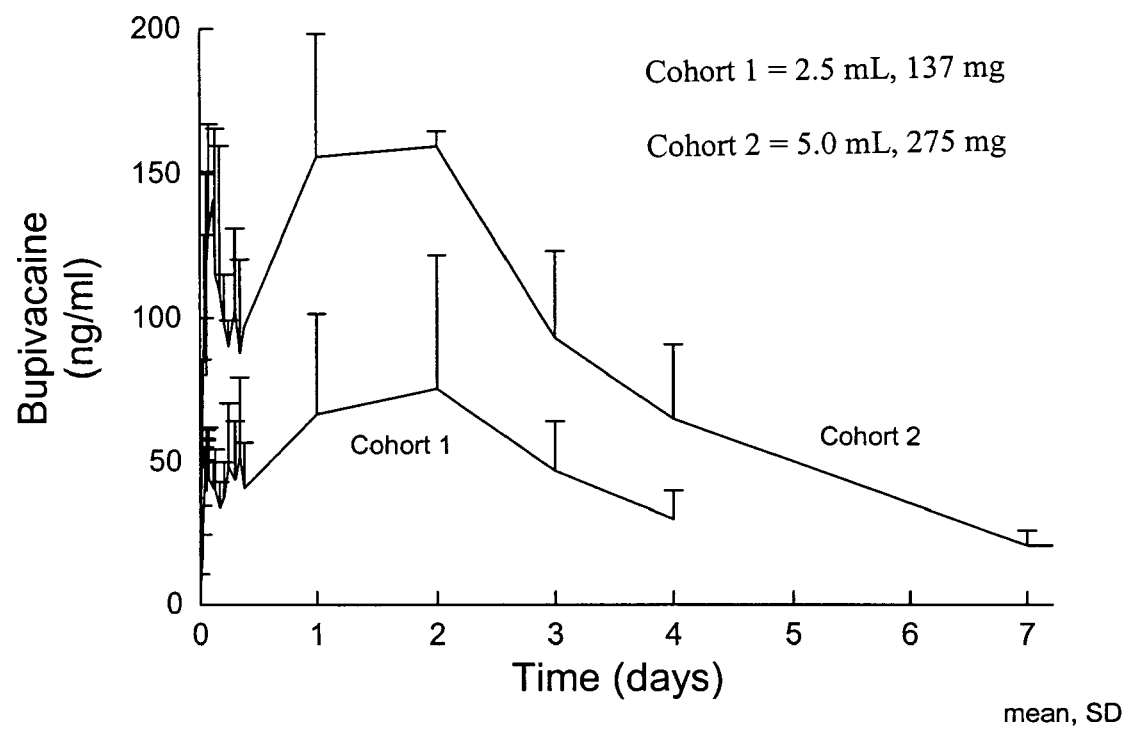
FIG. 1 depicts the mean plasma bupivacaine levels over 7 days (the pharmacodynamic results) from Example 3, wherein the Cohort 1 data is represented by the bottom curve, and the Cohort 2 data is represented by the top curve.
Figure 2:
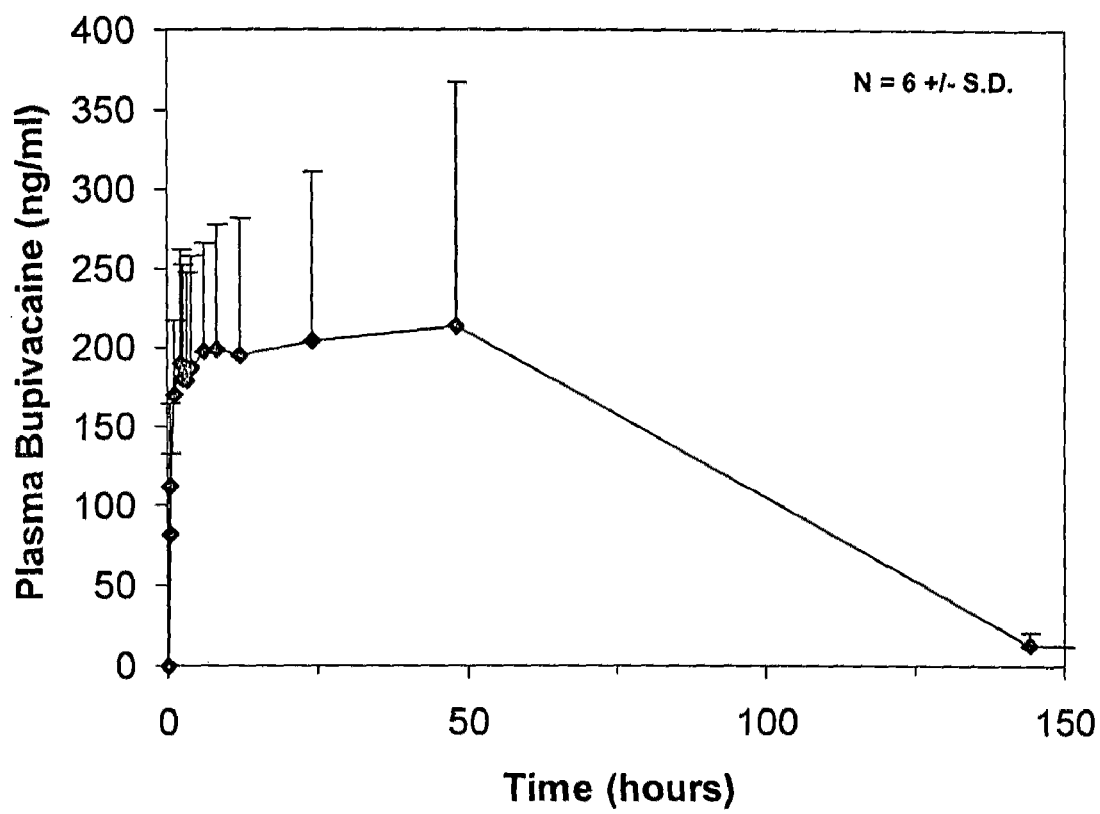
FIG. 2 depicts the mean plasma bupivacaine levels over 0-144 hours (the pharmacodynamic results) from Example 4, Cohort 1.
Figure 3:
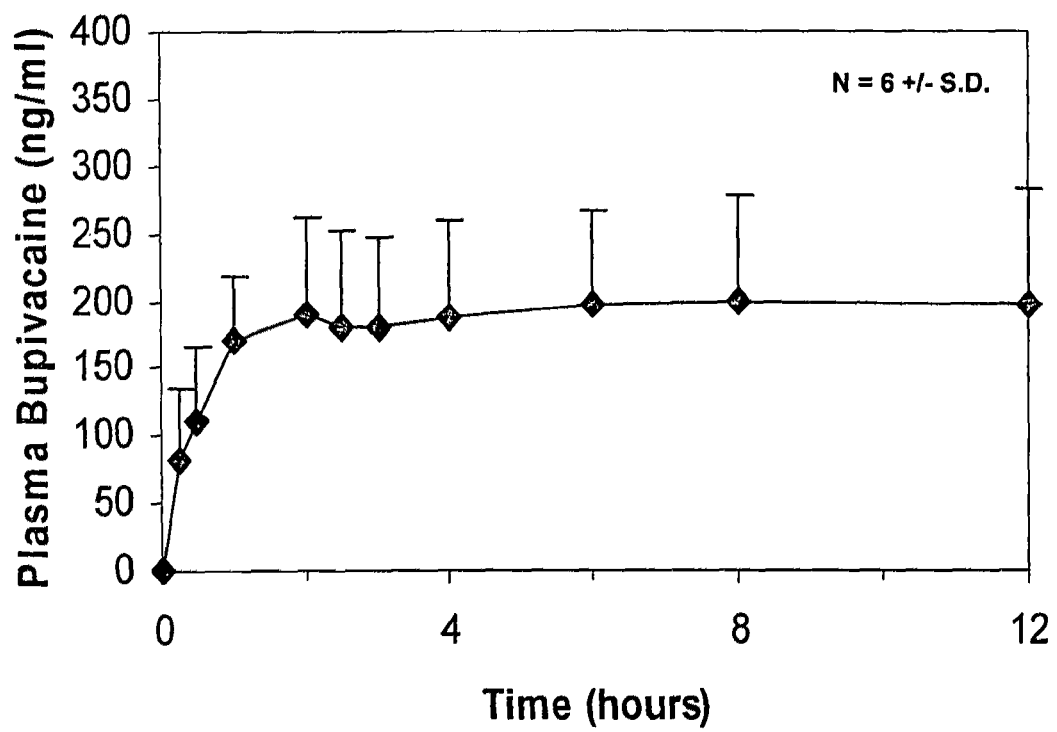
FIG. 3 depicts the mean plasma bupivacaine levels over 0-12 hours (the pharmacodynamic results) from Example 4, Cohort 1.
Figure 4:
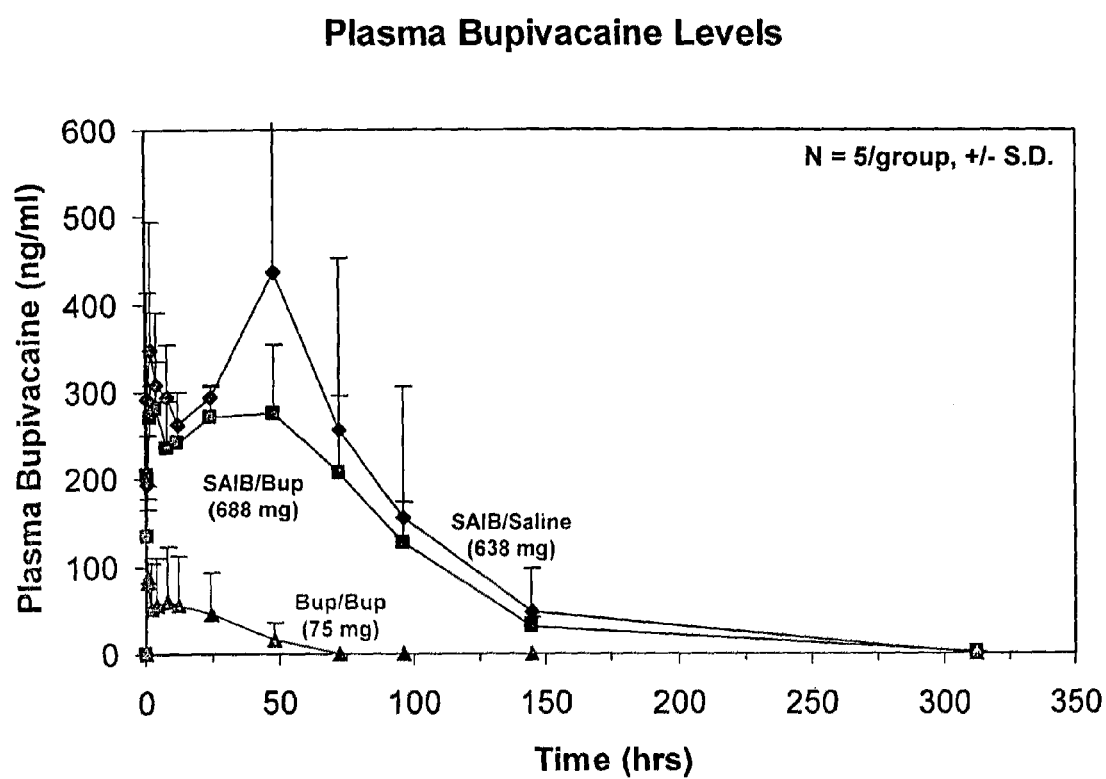
FIG. 4 depicts the mean plasma bupivacaine levels over 0-300 hours (the pharmacodynamic results) from Example 4, Cohort 2, where the subgroup 3 data is represented by the bottom curve (?), the subgroup 2 data is represented by the middle curve (?), and the subgroup 1 data is represented by the top curve (?).
Figure 5:
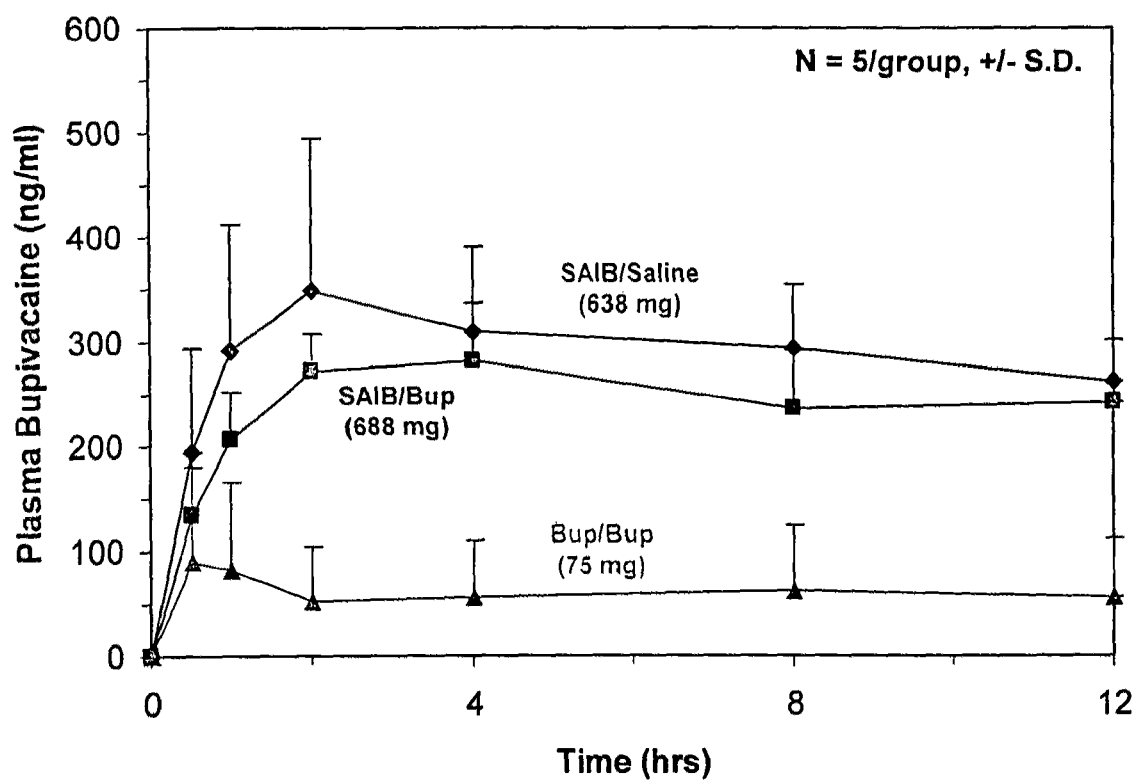
FIG. 5 depicts the mean plasma bupivacaine levels over 0-12 hours (the pharmacodynamic results) from Example 4, Cohort 2, where the subgroup 3 data is represented by the bottom curve (?), the subgroup 2 data is represented by the middle curve (?), and the subgroup 1 data is represented by the top curve (?).

Before describing the present invention in detail, it is to be understood that this invention is not limited to particularly exemplified carrier materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a non-polymeric carrier" includes a mixture of two or more such carriers, reference to "a solvent" includes a mixture of two or more such carriers, reference to "an anesthetic" includes mixtures of two or more such agents, and the like.

It is an object of the present invention to provide a long-acting controlled release system that releases an anesthetic over a prolonged period of time, sufficient to provide a local anesthetic effect at a site of administration for at least about 24 hours after administration, preferably at least about 36 to 48 hours after administration, and more preferably at least about 48 to 72 hours after administration. It is also an object of the present invention that release of the active anesthetic agent from the long-acting anesthetic composition occurs without an initial burst. It is a further object of the present invention that the composition releases the active anesthetic agent from the long-acting anesthetic composition to provide a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL.

It is also an object of the present invention to provide a composition containing an anesthetic and a pharmaceutically acceptable non-polymeric carrier. The non-polymeric carrier controls release of the anesthetic to provide an anesthetic effect characterized by sustained local anesthesia after administration to a subject without an initial burst and a duration of at least about 24 hours after administration, preferably at least about 36 to 48 hours after administration, and more preferably at least about 48 to 72 hours after administration.

It is also an object of the present invention to provide a composition containing an anesthetic and a pharmaceutically acceptable non-polymeric carrier. The non-polymeric carrier controls release of the anesthetic to provide an anesthetic effect characterized by sustained local anesthesia after administration to a subject, wherein the composition provides a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL.

It is a related object of the invention to provide a composition containing a first anesthetic, a second anesthetic, and a pharmaceutically acceptable non-polymeric carrier. In the composition, the second anesthetic is a solvent for the first anesthetic and provides an initial anesthetic effect upon administration to a subject. The non-polymeric carrier controls release of the first anesthetic to provide a subsequent anesthetic effect characterized by sustained local anesthesia having an onset within about 2 hours of administration to a subject without an initial burst and a duration of at least about 24 hours after administration, preferably at least about 36 to 48 hours after administration, and more preferably at least about 48 to 72 hours after administration.

It is also a related object of the invention to provide a composition comprising a non-polymeric, non-water soluble high viscosity liquid carrier material ("HVLCM") having a viscosity of at least 5,000 cP at 37° C. that does not crystallize neat under ambient or physiological conditions, a first anesthetic and a second anesthetic. Here again the second anesthetic is a solvent for the first anesthetic and provides an initial anesthetic effect upon administration to a subject. The HVLCM controls release of the first anesthetic to provide a subsequent anesthetic effect characterized by sustained local anesthesia having an onset within about 2 hours of administration to a subject without an initial burst and a duration of at least about 24 hours after administration, preferably at least about 36 to 48 hours after administration, and more preferably at least about 48 to 72 hours after administration.

It is a further related object of the invention to provide a composition comprising a non-polymeric, non-water soluble high viscosity liquid carrier material ("HVLCM") having a viscosity of at least 5,000 cP at 37° C. that does not crystallize neat under ambient or physiological conditions, a first anesthetic and a second anesthetic. Here again the second anesthetic is a solvent for the first anesthetic and provides an initial anesthetic effect upon administration to a subject. The HVLCM controls release of the first anesthetic to provide a subsequent anesthetic effect characterized by sustained local anesthesia, and the composition provides a sustained mean steady state plasma concentration ($C_{ss}$) of the anesthetic of at least about 200 ng/mL for a period of at least about 24 hours when the composition is administered subcutaneously, preferably at least about 250 ng/mL, or at least about 300 ng/mL, or at least about 350 ng/mL.

It is a further object of the invention to provide a method for providing an anesthetic effect at a site in a subject. The method comprises administering a composition at, near, in, or adjacent to the site, where the composition includes an anesthetic and a pharmaceutically acceptable non-polymeric carrier. The non-polymeric carrier controls release of the anesthetic to provide an anesthetic effect characterized by sustained local anesthesia after administration to the subject without an initial burst and having a duration of at least about 24 hours after administration.

It is yet a further object of the invention to provide a method for providing an anesthetic effect at a site in a subject. The method comprises administering a composition at, near, in, or adjacent to the site, where the composition includes an anesthetic and a pharmaceutically acceptable non-polymeric carrier. The non-polymeric carrier controls release of the anesthetic to provide an anesthetic effect characterized by sustained local anesthesia after administration to the subject, and the composition provides a sustained mean steady state plasma concentration ($C_{ss}$) of the anesthetic of at least about 200 ng/mL for a period of at least about 24 hours when the composition is administered subcutaneously.

It is a still further object of the invention to provide a method for providing an anesthetic effect at a site in a subject. The method comprises administering a composition at, near, in, or adjacent to the site, where the composition includes a first anesthetic, a second anesthetic, and a pharmaceutically acceptable non-polymeric carrier. The second anesthetic is a solvent for the first anesthetic and provides an initial anesthetic effect at the site upon administration. The non-polymeric carrier controls release of the first anesthetic to provide a subsequent anesthetic effect characterized by sustained local anesthesia at the site having an onset within about 2 hours of administration without an initial burst and a duration of at least about 24 hours after administration, preferably at least about 36 to 48 hours after administration, and more preferably at least about 48 to 72 hours after administration.

It is also an object of the invention to provide a method for providing an anesthetic effect at a site in a subject. The method comprises administering a composition at, near, in, or adjacent to the site, where the composition includes a first anesthetic, a second anesthetic, and a pharmaceutically acceptable non-polymeric carrier. The second anesthetic is a solvent for the first anesthetic and provides an initial anesthetic effect at the site upon administration. The non-polymeric carrier controls release of the first anesthetic to provide a subsequent anesthetic effect characterized by sustained local anesthesia at the site, and the composition provides a sustained mean steady state plasma concentration ($C_{ss}$) of the anesthetic of at least about 200 ng/mL for a period of at least about 24 hours when the composition is administered subcutaneously.

The phrase "without an initial burst," as used herein, intends that the particular agent being referred to does not release from the composition upon normal administration and become pharmacologically available in an appreciable amount during a predetermined initial period. The presence and level of an initial burst of an agent from a given composition can be readily determined by the skilled artisan employing standard pharmacological testing techniques well known in the art. Suitable in vitro burst release characterization methods include the USP II Paddle Method, using standard buffer, mixing and heat conditions. The burst release characteristics of a given composition can also readily be determined using standard in vivo testing, such as by monitoring plasma concentrations of the agent of interest in an animal subject, over a given time period. In the compositions of the present invention, preferably less than about 40 to 60% of the anesthetic agent is released within the first 24 hours, more preferably less than about 30 to 50%, and even more preferably less than about 20 to 40% is released within this initial time period. In certain other preferred embodiments, less than about 5 to 10% of the anesthetic agent is released within the first hour, more preferably less than about 3 to 7% is released within this initial time period.

Accordingly, the compositions of the present invention will contain at least one anesthetic agent in a controlled release system that releases an anesthetic over a prolonged period of time. In certain embodiments, the anesthetic is present in the instant compositions in an amount of from about 95 to about 1 percent by weight relative to the total weight of the composition (wt %), in an amount of from about 30 to 1 wt %, in an amount of from about 25 to 5 wt %, or in an amount of about 20 to 10 wt %, depending on the identity of the anesthetic and the intended use thereof.

As used herein, the term "anesthetic" intends any agent that provides reversible local numbness, pain relief, blocks impulse conduction along nerve axions and other excitable membranes, such as a regional blockage of nociceptive pathways (afferent and/or efferent), analgesia, and/or anesthesia. See, e.g., Strichartz, G. R. (Ed.) Local Anesthetics, Handbook of Experimental Pharmacology, vol. 81, Springer, Berlin/New York, (1987). The term also includes any agent which, when locally administered provides localized (regional) full or partial inhibition of sensory perception and/or motor function. Examples of commonly used agents suitable for use as anesthetics in the practice of the invention include, but are not limited to ambucaine, amolanone, amylcaine, benoxinate, benzyl alcohol, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, etidocaine, euprocin, fenalcomine, formocaine, hexylcaine, hydroxyteteracaine, isobuanine, isobutyl p-aminobenzoate, leucinocaine, levobupivacaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocalne, procaine, propanocaine, proparacaine, propipocaine, propoxycaine, pseudococaine, pyrrocaine, ropivacaine, salicyl alcohol, tetracaine, tolycaine, trimecaine, xylocalne, zolamine, anesthetically active derivatives, analogs and any pharmaceutically acceptable salt thereof, and any mixture thereof.

The amide- and ester-type of local anesthetics are preferred for use herein. Amide-type local anesthetics are characterized by having an amide functionality, while ester-type local anesthetics contain an ester functionality. Preferred amide-type local anesthetics include lidocaine, bupivacaine, prilocalne, mepivacaine, etidocaine, ropivacaine and dibucaine. Preferred ester-type local anesthetics include tetracaine, procaine, benzocaine and chloroprocaine. The most preferred local anesthetic is bupivacaine.

The anesthetic agent is provided in the composition in a neutral form, as a free base form, or in the form of a pharmaceutically acceptable salt. The term "pharmaceutically acceptable salt," as used herein, intends those salts that retain the biological effectiveness and properties of neutral anesthetics and are not otherwise unacceptable for pharmaceutical use. Pharmaceutically acceptable salts include salts of acidic or basic groups, which groups may be present in the anesthetic agents. Those anesthetic agents that are basic in nature are capable of forming a wide variety of salts with various inorganic and organic acids. Pharmaceutically acceptable acid addition salts of basic anesthetics suitable for use herein are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Anesthetic agents that include an amino moiety may form pharmaceutically acceptable salts with various amino acids, in addition to the acids mentioned above. Suitable base salts can be formed from bases which form non-toxic salts, for example, aluminium, calcium, lithium, magnesium, potassium, sodium, zinc and diethanolamine salts. See, e.g., Berge et al. (1977) J. Pharm. Sci. 66:1-19.

The ability of an anesthetic agent to provide a condition of sustained local anesthesia refers to the ability of the subject agent to establish an assessable state of localized (regional) full or partial inhibition of sensory perception and/or motor function. Numerous methods and tools for making such an assessment will readily occur to the skilled artisan. With regard to non-human animal subjects, these methods include measurement of spontaneous locomotion in test rats (using, for example, commercially available equipment and software from Med Associates Inc., St. Albans, Vt.), where data can be collected on total distance traveled, ambulatory counts, stereotypy, rearing, time spent in the various motions and time spent at rest for test subjects; visualization of pin prick reaction in rats; and the rat hotplate foot withdrawal model, e.g., according to the procedure described in detail in IACUC No 9511-2199.

Sensory testing in human subjects is also a useful way of assessing local anesthetic effect. Testing is often focused on three general areas, mechanical testing (pin prick, von Frey Hairs), thermal (warm, hot, cool) and tactile testing (touch). Such testing techniques are described in the literature. See, for example, Dahl, et al. (1993) Pain 53:43-51; Moiniche, et al. (1993) Brit. J. of Anaesthesia 71:201-205; Moiniche, et al. (1993) Regional Anesthesia 18:300-303; Pedersen, et al. (1996) Anesthesiology 84(5):1020-1026; Pedersen, et al. (1996) Brit. J. of Anaesthesia 76(6):806-810; and Pedersen, et al. (1998) Pain 74:139-151. For example, the local anesthetic activity of a test agent can be examined with reference to onset, peak density and duration of effect using specific modalities: 1) mechanical sensory testing (mechanical pain detection threshold using von Frey hairs; 2) suprathreshold (mechanical) testing using a single von Frey hair; 3) thermal sensory testing (warm detection threshold); 4) heat pain detection threshold; 5) suprathreshold (heat) testing; 6) cool detection threshold; and 7) tactile sensory testing (mechanical touch detection threshold). These data are indicative of the subject experiencing local pain relief, local numbness, and or local nerve blockade in response to administration of a test anesthetic agent. Pain response can be characterized using a Verbal Rank Scale of 0-10 (e.g., where 0=no pain, and 10=the worst imaginable pain) or a Visual Analog Scale from 0 to 100 mm (e.g., where 0=no pain, and 100 mm=worst imaginable pain).

With regard to selection of a particular anesthetic agent, the skilled artisan will also recognize that the pharmacological properties of each candidate agent will vary, for example, with respect to onset and intensity of anesthetic effect, duration and the like. Certain agents may provide a mild anesthetic effect, having a fairly rapid onset of activity, but a short duration. Such agents can be used with the compositions of the present invention in order to provide an "initial anesthetic effect," where they are typically paired with a different anesthetic agent that provides a "sustained local anesthesia," characterized by a more gradual onset of activity, but a stronger effect and one of longer duration. An example of an anesthetic that can be used to provide an initial anesthetic effect is benzyl alcohol. An example of an anesthetic that can be used to provide a sustained local anesthesia is bupivacaine. Still further agents that can be used to provide an initial anesthetic effect can include organic materials commonly used as solvents and/or penetration agents, such as ethanol, dimethyl sulfoxide, N-methylpyrrolidone, polyethylene glycol and certain fatty acid esters. These and other similar agents can provide a very mild initial anesthetic effect, for example, when applied they can cool or otherwise desensitize/numb a tissue site, thereby partially inhibiting sensory perception at that site. Whenever an agent is used in the practice of the invention in order to provide an initial anesthetic effect, the agent is provided in a suitable composition in an amount sufficient to provide the subject effect, and in such as way that the agent is able to be released from the composition quickly in order to provide the intended effect. Assembly of such suitable compositions (containing an agent for providing an initial anesthetic effect) is within the skill of the art when taken in combination with the guidance and teaching provided by the instant specification.

In certain embodiments of the invention, a composition is provided that includes two anesthetic agents, a first anesthetic and a second anesthetic, wherein the second anesthetic agent is a solvent for the first anesthetic agent. In these particular compositions, the second anesthetic agent is typically used to provide an initial anesthetic effect, and the first anesthetic agent is used to provide a subsequent anesthetic effect characterized by sustained local anesthesia, having an onset within about 2 hours of administration to a subject without an initial burst, and a duration of at least about 24 hours after administration, or even longer. In certain preferred embodiments, the first anesthetic agent provides the sustained local anesthesia with an onset within about 1 to 2 hours of administration, and in other preferred embodiments, the first anesthetic agent provides the sustained local anesthesia with an onset within about 30 minutes to 1 hour of administration. In certain other embodiments, the second anesthetic is also a solvent for the controlled release carrier system.

An anesthetic agent will serve as a solvent for another anesthetic agent herein when one agent is at least partially dissolved in the other solvent agent in the manufacture of the composition. In addition, the anesthetic solvent is present in the composition in an amount sufficient to provide both an initial anesthetic effect and at least partially dissolve the other anesthetic agent. In certain embodiments, the second anesthetic is thus present in an amount of from about 95 to about 1 percent by weight relative to the total weight of the composition (wt %), or in an amount of from about 75 to 10 wt %, or in an amount of from about 50 to 15 wt %.

A number of suitable anesthetic agents that also serve as solvents for other anesthetic agents can be used in the practice of the invention. Suitable agents include aromatic alcohols, acids and acid derivatives, and combinations thereof. A particularly preferred anesthetic agent that can be used as a solvent for an additional anesthetic is benzyl alcohol.

The controlled release carrier systems employed in the compositions of the present invention are classified as non-polymeric carriers. A pharmaceutically acceptable non-polymeric carrier is typically biocompatible, and preferably biodegradable, bioerodible, or bioabsorbable. A substance is biocompatible if it and any its degradation products present no significant, deleterious or untoward effects, nor cause substantial tissue irritation or necrosis when administered to living tissue. "Biodegradable" or "bioerodible," used interchangeably herein, means the subject non-polymeric material will degrade or erode in vivo to form smaller chemical species, wherein such degradation can result, for example, from enzymatic, chemical, and physical processes. "Bioabsorbable" means that a given nonpolymeric material can be broken down and absorbed within an animal subject's body, for example, by a cell, tissue or the like.

The non-polymeric carrier material is used to control release of at least one anesthetic agent from the compositions of the present invention, in such a way as to provide a sustained local anesthesia having an onset within about 2 hours of administration and a duration of at least about 24 hours or longer. In some compositions of the present invention, the non-polymeric carrier material is sufficient to provide either a first order controlled-release profile of the at least one anesthetic, or a pseudo-zero order release profile. Accordingly, the non-polymeric carrier will be present in the composition in an amount of from about 99.5 to about 1 percent by weight relative to the total weight of the composition (wt %), or in an amount of from about 95 to 10 wt %, or in an amount of from about 75 to 25 wt %.

Selection of a suitable non-polymeric carrier is within the general skill in the art, using the teaching and guidance provided by the instant disclosure and specification. For example, numerous pharmaceutically acceptable non-polymeric carrier systems are available to the skilled artisan to produce liquid, spray, cream, lotion, ointment, gel, slurry, oil, emulsion, microemulsion, solid, plaster, film, particle, microparticle, powder or other suitable form pharmaceutical compositions. These and other carrier systems are described, for example, in Remington's Pharmaceutical Sciences, $16^{th}$ Edition, 1980 and $17^{th}$ Edition, 1985, both published by Mack Publishing Company, Easton, Pa.

The compositions of the present invention may further include one or more additional component, for example pharmaceutically acceptable excipient materials that can act as dispersing agents, bulking agents, binders, carriers, stabilizers, glidants, antioxidants, pH adjusters, anti-irritants, and the like. The skilled artisan will appreciate that certain excipient materials can serve several of the above-referenced functions in any particular formulation. Thus, any number of suitable excipient materials can be mixed with or incorporated into the compositions of the present invention to provide bulking properties, alter active agent release rates, increase or impede water uptake, control pH, provide structural support, facilitate manufacturing processes and other uses known to those skilled in the art. The term "excipient" generally refers to a substantially inert material that is nontoxic and does not interact with other components of the composition in a deleterious manner. The proportions in which a particular excipient may be present in the composition depend upon the purpose for which the excipient is provided and the identity of the excipient.

For example, suitable excipients that can also act as stabilizers for active agents include pharmaceutical grades of dextrose, sucrose, lactose, trehalose, mannitol, sorbitol, inositol, dextran, and the like. Such stabilizers may thus be a saccharide such as a monosaccharide, a disaccharide, a polysaccharide or a sugar alcohol. Other suitable excipients include starch, cellulose, sodium or calcium phosphates, calcium sulfate, citric acid, tartaric acid, glycine, and combinations thereof. Examples of hydrophobic excipients that can be added to slow hydration and dissolution kinetics include fatty acids and pharmaceutically acceptable salts thereof (e.g., magnesium stearate, steric acid, zinc stearate, palimitic acid, and sodium palitate).

It may also be useful to employ a charged lipid and/or detergent excipient in the compositions of the present invention. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g. Brij; pharmaceutically acceptable fatty acid esters, e.g., lauryl sulfate and salts thereof; ampiphilic surfactants (glycerides, etc.); and like materials.

Other excipient materials can be added to alter porosity, for example, materials like sucrose, dextrose, sodium chloride, sorbitol, lactose, polyethylene glycol, mannitol, fructose, polyvinyl pyrrolidone or appropriate combinations thereof. Additionally, the anesthetic agent or agents may be dispersed with oils (e.g., sesame oil, corn oil, vegetable), or a mixture thereof with a phospholipid (e.g., lecitin), or medium chain fatty acid triglycerides (e.g., Miglyol 812) to provide an oily suspension.

Still further excipeint materials that can be incorporated into the compositions of the present invention include diluents of various buffer content (e.g., Tris-HCl, acetate); pH and ionic strength altering agents; additives such as antioxidants (e.g., ascorbic acid, glutathione, sodium metabisulfite); preservatives (e.g., Thimersol, benzyl alcohol, methyl paraben, propyl paraben); and dispersing agents such as water-soluble polysaccharides (e.g., mannitol, lactose, glucose, starches), hyaluronic acid, glycine, fibrin, collagen and inorganic salts (e.g., sodium chloride).

In certain embodiments of the invention, the non-polymeric carrier is substantially insoluble in water or in an aqueous biological system. Exemplary such non-polymeric carrier materials include, but are not limited to: sterols such as cholesterol, stigmasterol, β-sitosterol, and estradiol; cholestery esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Certain preferred non-polymeric carriers include cholesterol, glyceryl monostearate, glycerol tristearate, stearic acid, stearic anhydride, glyceryl monocleate, glyceryl monolinoleate, and acetylated monoglycerides.

If one of the above-noted non-polymeric carrier materials is selected for use in a composition of the present invention, it will typically be combined with a compatible and suitable organic solvent for the carrier material to form a composition having a consistency ranging from watery to viscous to a spreadable putty or paste. The consistency of the composition will vary according to factors such as the solubility of the non-polymeric carrier in the solvent, the concentration of the non-polymeric carrier, the concentration of the anesthetic agent and/or the presence of additional anesthetic agents, additives and excipients. The solubility of a non-polymeric carrier in a particular solvent will vary according to factors such as its crystallinity, hydrophilicity, ionic character and lipophilicity. Accordingly, the ionic character and the concentration of the non-polymeric carrier in the solvent can be adjusted to achieve the desired solubility. Preferred non-polymeric carrier materials are those that have low crystallinity, nonpolar characteristics, and are more hydrophobic.

Suitable organic solvents for use in the compositions are generally those that are biocompatible, pharmaceutically acceptable, and will at least partially dissolve the non-polymeric carrier. The organic solvent will further have a solubility in water ranging from miscible to soluble to dispersible. In certain embodiments, the solvent is selected such that it is capable of diffusing, dispersing, or leaching away from the composition in situ in an aqueous system and into fluids found at the administration site, thereby forming a solid implant. Preferably, the solvent has a Hildebrand (HLB) solubility ratio of from about 9-13 $(cal/cm^3)^{1/2}$. Preferably, the degree of polarity of the solvent is effective to provide at least about 5% solubility in water.

Suitable organic solvents thus include, but are not limited to: substituted heterocyclic compounds such as N-methyl-2-pyrrolidone (NMP) and 2-pyrrolidone (2-pyrol); esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol); Solketal; dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof. Preferred solvents include N-methyl-2-pyrrolidone, 2-pyrrolidone, dimethylsulfoxide, ethyl lactate, propylene carbonate, glycofurol, glycerol formal, and isopropylidene glycol.

The organic solvent will be provided in the composition in an amount of from about 99.5 to about 1 percent by weight relative to the total weight of the composition (wt %), in an amount of from about 95 to 10 wt %, in an amount of from about 75 to 25 wt %, or in an amount of from about 60 to 40 wt %, depending upon the selected non-polymeric carrier, organic solvent, anesthetic agent, additive and/or excipient being used in the composition. In certain embodiments, the organic solvent diffuses or leaches away from the composition into an aqueous medium upon placement within a biological system, whereby the non-polymeric carrier material coagulates to form a solid matrix. Preferably, the non-polymeric carrier solidifies in situ to form a solid matrix within about 1-5 days after administration (implantation), preferably within about 1-3 days, preferably within about 2 hours.

A number of suitable additives may be included with the composition in order to impart selected characteristics upon the composition. For example, the may include a minor amount of a biodegradable thermoplastic polymer such as a polylactide, polycaprolactone, polyglycolide, or copolymer thereof, in order to provide a more coherent solid implant or a composition with greater viscosity so as to hold it in place while it solidifies. Such thermoplastic polymers are disclosed in U.S. Pat. No. 4,938,763 to Dunn et al.

Optionally, a pore-forming agent can be included in the composition. The pore-forming agent can be any organic or inorganic, pharmaceutically-acceptable substance that is substantially soluble in water or body fluid, and will dissipate from the non-polymeric carrier material and/or the solid matrix of an implant into surrounding body fluid at the implant site. The pore-forming agent may preferably be insoluble in the organic solvent to form a uniform mixture with the non-polymeric carrier material. The pore-forming agent may also be a water-immiscible substance that rapidly degrades to a water-soluble substance. In certain compositions, the pore-forming agent is combined with the non-polymeric carrier and organic solvent in admixture. Suitable pore-forming agents that can be used in the composition include, for example, sugars such as sucrose and dextrose, salts such as sodium chloride and sodium carbonate, polymers such as hydroxylpropylcellulose, carboxymethylcellulose, polyethylene glycol and polyvinylpyrrolidone, and the like. Solid crystals that will provide a defined pore size, such as salt or sugar, are preferred.

In other embodiments of the present invention, compositions are provided wherein the non-polymeric carrier is a liquid. The liquid non-polymeric carrier is preferably a high viscosity liquid carrier material ("HVLCM") to be non-water soluble, and has a viscosity of at least 5,000 cP, (and optionally at least 10,000, 15,000; 20,000; 25,000 or even 50,000 cP) at 37° C. that does not crystallize neat under ambient or physiological conditions. The term "non-water soluble" refers to a material that is soluble in water to a degree of less than one percent by weight under ambient conditions. The term "non-polymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "nonpolymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered nonpolymeric as that term is used herein.

In a particular embodiment, the HVLCM decreases in viscosity, in some cases significantly, when mixed with a solvent to form a low viscosity liquid carrier material ("LVLCM") that can be administered using standard medical devices. The LVLCM composition is typically easier to place in the body than a HVLCM composition, because it flows more easily into and out of syringes or other implantation means. It also can easily be formulated as an emulsion. The LVLCM can have any desired viscosity, but its viscosity is generally lower than the corresponding HVLCM. As an example, viscosity ranges for the LVLCM of less than approximately 6,000 cP, less than approximately 4,000 cP, less than approximately 1,000 cP, or less than 200 cP, are typically useful for in vivo applications.

The particular HVLCM used in the compositions of the invention can be one or more of a variety of materials. Suitable materials include nonpolymeric esters or mixed esters of one or more carboxylic acids. In a particular embodiment, the ester is formed from carboxylic acids that are esterified with a polyol having from about 2 to about 20 hydroxy moieties, and which may include 1 to about 20 etherified polyols. Particularly suitable carboxylic acids for forming the acid moiety of the ester of the HVLCM include carboxylic acids having one or more hydroxy groups, e.g., those obtained by ring opening alcoholysis of lactones, or cyclic carbonates or by the alcoholysis of carboxylic acid anhydrides. Amino acids are also suitable for forming esters with the polyol. In a particular embodiment, the ester or mixed ester contains an alcohol moiety having one or more terminal hydroxy moieties that have been esterified with one or more carboxylic acids obtained by alcoholysis of a carboxylic acid anhydride, such as a cyclic anhydride.

Nonlimiting examples of suitable carboxylic acids that can be esterified to form the HVLCM include glycolic acid, lactic acid, ε-hydroxycaproic acid, serine, and any corresponding lactones or lactams, trimethylene carbonate, and dioxanone. The hydroxy-containing acids may themselves be further esterified through the reaction of their hydroxy moieties with additional carboxylic acid, which may be the same as or different from other carboxylic acid moieties in the material. Suitable lactones include, but are not limited to, glycolide, lactide, ε-caprolactone, butyrolactone, and valerolactone.

Suitable carbonates include but are not limited to trimethylene carbonate and propylene carbonate.

The alcohol moiety of the ester or mixed ester may be derived from a polyhydroxy alcohol having from about 2 to about 20 hydroxy groups, and as indicated above, may be formed by etherifying 1 to 20 polyol molecules. Suitable alcohol moieties include those derived by removing one or more hydrogen atoms from: monofunctional $C_1$-$C_{20}$ alcohols, difunctional $C_1$-$C_{20}$ alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, the alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, fructose, sucrose, glucuronic acid, polyglycerol ethers containing from 1 to about 10 glycerol units, polyethylene glycols containing 1 to about 20 ethylene glycol units.

In particular embodiments of the invention, at least one of the carboxylic acid moieties of the esters or mixed esters of the HVLCM comprise at least one oxy moiety In an even more particular embodiment, each of the carboxylic acid moieties comprise at least one oxy moiety.

In another particular embodiment, at least one of the carboxylic acid moieties of the esters or mixed esters of the invention contains 2 to 4 carbon atoms. In an even more particular embodiment, each of the carboxylic acid moieties of the esters or mixed esters of the invention contains 2 to 4 carbon atoms.

In another more particular embodiment of the invention, at least one of the carboxylic acid moieties of the ester or mixed ester of the invention has 2 to 4 carbon atoms and contains at least one oxy moiety. In another more particular embodiment of the invention, each of the carboxylic acid moieties of the ester or mixed ester of the invention has 2 to 4 carbon atoms and contains at least one oxy moiety.

In a particular embodiment, the HVLCM may be sucrose acetate isobutyrate (SAIB) or some other ester of a sugar alcohol moiety with one or more alkanoic acid moieties.

In a particular embodiment, the invention includes compositions wherein the HVLCM has a structure selected from the group consisting of:

I:

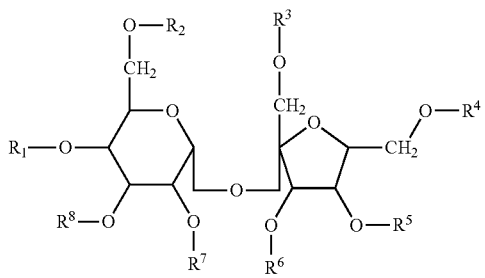

wherein $R^1$, $R^2$, $R^3$, $R^4$, $R^5$, $R^6$, $R^7$, and $R^8$ are independently selected from the group consisting of hydrogen, alkanoyl, hydroxy-substituted alkanoyl, and acyloxy-substituted alkanoyl;

wherein at least three of $R^1$, $R^2$, $R^3$, $R^4$, $R^5$, $R^6$, $R^7$, and $R^8$ are other than hydrogen; and wherein when $R^1$, $R^2$, $R^3$, $R^4$, $R^5$, $R^6$, $R^7$, and $R^8$ are selected from the group consisting of acetyl and isobutyryl, at least three of $R^1$, $R^2$, $R^3$, $R^4$, $R^5$, $R^6$, $R^7$, and $R^8$ are acetyl;

II:

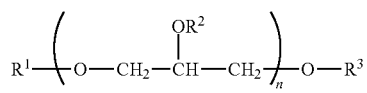

wherein $R^1$, $R^2$, and $R^3$ are independently selected from the group consisting of hydrogen, alkanoyl, hydroxy-substituted alkanoyl, and acyloxy-substituted alkanoyl and wherein n is between 1 and 20;

$$R^1\text{—}O\text{—}(CH_2)_n\text{—}O\text{—}R^2 \qquad \text{III}$$

wherein n is an integer between 4 and 8, and $R^1$ and $R^2$ are independently selected from the group consisting of hydrogen, alkanoyl, hydroxy-substituted alkanoyl, and acyloxy-substituted alkanoyl;

IV:

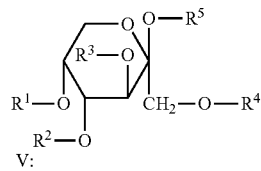

V:

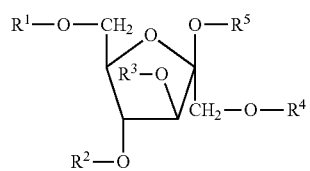

wherein in formulae IV and V, $R^1$, $R^2$, $R^3$, $R^4$, and $R^5$ are independently selected from the group consisting of hydrogen, alkanoyl, hydroxy-substituted alkanoyl, and acyloxy-substituted alkanoyl;

VI:

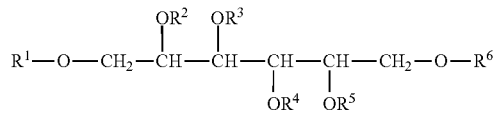

VII:

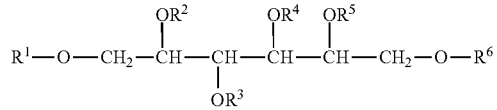

wherein in formulae VI and VII, $R^1$, $R^2$, $R^3$, $R^4$, $R^5$, and $R^6$ are independently selected from the group consisting of hydrogen, alkanoyl, hydroxy-substituted alkanoyl, and acyloxy-substituted alkanoyl;

VIII:

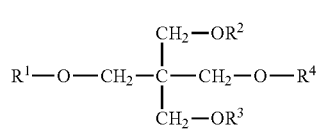

wherein $R^1$, $R^2$, $R^3$, and $R^4$ are independently selected from the group consisting of hydrogen, alkanoyl, hydroxy-substituted alkanoyl, and acyloxy-substituted alkanoyl.

In each of formulae I through VIII, one or more of the alkanoyl, hydroxy-substituted alkanoyl, and acyloxy-substituted alkanoyl groups may comprise alkanoyl moieties having 2 to 6 carbon atoms, including the carbonyl carbon. Moreover, in another more particular embodiment of the invention, each of formulae I through VIII comprise at least one hydroxy-substituted or acyloxy-substituted alkanoyl moiety. In an even more particular embodiment, at least one of these hydroxy-substituted or acyloxy-substituted alkanoyl moieties comprise alkanoyl moieties having 2 to 6 carbon atoms, including the carbonyl carbon.

The acyl groups forming the acyloxy substituents of the HVLCM may be any moiety derived from a carboxylic acid in accordance with the commonly accepted definition of the term "acyl." More particularly, the acyl groups of the compositions of the invention may be of the form $R^9CO—$, where $R^9$ is optionally oxy-substituted alkyl of 2-6 carbon atoms. This oxy-substitution may take the form of hydroxy substitution, or substitution with additional acyl moieties. For example $R^9$ may be an oligomer of oxy-substituted carboxylic acids, linked by ester bonding between the hydroxy of one acid and the carboxy of another acid. In a more particular example, $R^9$ may comprise 1 to 5 lactide or glycolide units, where a lactide unit contains two lactic acid moieties esterified together and a glycolide unit contains two glycolic acid moieties esterified together. Alternatively, $R^9$ may contain mixed lactide and glycolide units, or may contain mixed lactic acid and glycolic acid, without the presence of lactide or glycolide units.

Particular HVLCM materials include components according to formulae II or III, wherein $R^1$, $R^2$, and $R^3$ are independently lactoyl, polylactoyl, ϵ-caproyl, hydroxyacetyl, or polyhydroxyacetyl, in particular, polylactoyl and ϵ-caproyl, or polylactoyl and polyhydroxyacetyl.

The use of relatively small chain (2 to 6 carbon atoms), oxy-substituted carboxylic acid moieties in the ester or mixed ester of the invention is advantageous. When these acid moieties are present in the form of oligomeric esters (i.e., a subsequent acid moiety joined to the previous acid moiety through esterification of the subsequent carboxy with the previous oxy), hydrolysis of the material is considerably easier than for oligomers made with more than 6 carbon atoms because the material is more hydrophilic. In general, for drug delivery it is desired that the HVLCM be water insoluble, but it may be somewhat hydrophilic. In general, HVLCMs synthesized with more hydrophilic units (as determined by a higher O:C ratio) will be expected to absorb water more rapidly and degrade more quickly. For example, a HVLCM made by covalently linking 4 moles of glycolide to one mole of glycerol will be expected to absorb water more rapidly and degrade more quickly than a HVLCM made by covalently linking 2 moles of glycolide and 2 moles of lactide to one mole of glycerol. Similar increases can be expected for more flexible molecules and for more branched, spherical molecules based on free volume arguments. Use of flexible and branched molecules may also have the benefit of lowering the viscosity of the LVLCM. Using carboxylic acids and/or polyols of different chain length and using carboxylic acids having oxy-substitution allows a precise control of the degree of hydrophilicity and of the solubility of the resulting ester. These materials are sufficiently resistant to dissolution in vivo that they are able to provide a controlled release of a carried anesthetic agent into the body accompanied or followed by oxy bonds hydrolyzing in vivo.

In an even more particular embodiment, the HVLCM excludes the acetate and isobutyrate ester of sucrose having a ratio of acetate to isobutyrate acid moieties of 2:6. However, sucrose acetate isobutyrate ester having a ratio of acetate to isobutyrate moieties of 2:6 is included within the scope of the invention for use in aerosol formulations. This material can be made according to the procedures described in U.S. Pat. No. 2,931,802.

In general, suitable HVLCM esters can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate can be used. The heated reaction mixture, with or without catalyst, is heated with stirring then dried, e.g., under vacuum, to remove any un-reacted starting materials and produce a liquid product. Sucrose acetate isobutyrates can be made by following the procedures described in U.S. Pat. No. 2,931,802.

In this regard, the polyol can be viewed as an oligomerization initiator, in the sense that it provides a substrate for esterification of carboxylic acids, in particular, of oligomers of lactide, glycolide, or other esterified hydroxy-substituted carboxylic acids.

In certain embodiments, the HVLCM can be mixed with a viscosity-lowering solvent to form a lower viscosity liquid carrier material (LVLCM), which can then be mixed with the one or more anesthetic agent to be delivered, prior to administration. These solvents can be water soluble, non-water soluble, or water miscible, and can include, acetone, benzyl alcohol, benzyl benzoate, N-(betahydroxyethyl) lactamide-butylene glycol, caprolactam, caprolactone, corn oil, decylmethylsulfoxide, dimethyl ether, dimethyl sulfoxide, 1-dodecylazacycloheptan-2-one, ethanol, ethyl acetate, ethyl lactate, ethyl oleate, glycerol, glycofurol (tetraglycol), isopropyl myristate, methyl acetate, methyl ethyl ketone, N-methyl-2-pyrrolidone, MIGLYOLs® (esters of caprylic and/or capric acids with glycerol or alkylene glycols, e.g., MIGLYOL® 810 or 812 (caprylic/capric triglycerides), MIGLYOL® 818 (caprylic/capric/linoleic triglyceride), MIGLYOL® 829 (caprylic/capric/succinic triglyceride), MIGLYOL® 840 (propylene glycol dicaprylate/caprate)), oleic acid, peanut oil, polyethylene glycol, propylene carbonate, 2-pyrrolidone, sesame oil, SOLKETAL ([±]-2,2-dimethyl-1,3-dioxolane-4-methanol), tetrahydrofuran, TRANSCUTOL® (diethylene glycol monoethyl ether, carbitol), triacetin, triethyl citrate, diphenyl phthalate, and combinations thereof. Additionally, if the composition is to be applied as an aerosol, e.g. for topical application, the solvent may be or may include one or more propellants, such as CFC propellants like trichlorofluoromethane and dichlorofluoromethane, non-CFC propellants like tetrafluoroethane (R-134a), 1,1,1,2,3,3,3-heptafluoropropane (R-227), dimethyl ether, propane, and butane.

Particularly suitable solvents and/or propellants include benzyl benzoate, benzyl alcohol, triacetin, triethyl citrate, dimethyl sulfoxide, ethanol, ethyl lactate, glycerol, glycofurol (tetraglycol), N-methyl-2-pyrrolidone, MIGLYOL® 810, polyethylene glycol, propylene carbonate, 2-pyrrolidone, and tetrafluoroethane.

Other possible solvents include perfluorodecalin, perfluorotributylamine, methoxyflurane, glycerolformal, tetrahydrofurfuryl alcohol, diglyme, and dimethyl isosorbide.

When the composition is used as a LVLCM to administer the anesthetic agent, it should contain a solvent that the HVLCM is soluble in. In certain instances, the anesthetic agent is also soluble in the solvent. In still further instances, the solvent is a second anesthetic agent in which the first anesthetic agent is soluble. The solvent is preferably nontoxic and otherwise biocompatible.

In certain embodiments, the solvent is at least water soluble, so that it will diffuse quickly into bodily fluids or other aqueous environment upon administration, causing the composition to coagulate and/or become more viscous. In another embodiments, the solvent is not completely miscible with water or bodily fluids so that diffusion of the solvent from the composition, and the corresponding increase in viscosity of the composition, are slowed. Suitable solvents that have this property, at least to some extent, include benzyl benzoate, MIGLYOL® 810, benzyl alcohol, and triethylcitrate. Benzyl alcohol can be particularly suitable, as it also an anesthetic agent.

When esters of 1,6-hexanediol or glycerol are used as the HVLCM, some possible solvents are ethanol, N-methylpyrrolidone, propylene carbonate, and PEG 400.

The solvent is typically added to the compositions in an amount in the range from about 99.7 percent to about 0.5 percent by weight relative to the total weight of the composition (wt %), from about 95 percent to about 1 wt %, from about 75 to about 10 wt %, or from about 50 to 15 wt %. The solvent is typically present in the composition in an amount in the range from about 55 percent to 10 wt %.

In still further embodiments of the invention, the composition includes a material that is not miscible with the HVLCM, such that when combined with the HVLCM singularly or in combination with a solvent for the HVLCM, the resulting composition forms an emulsion. Such emulsions may contain the HVLCM in the dispersed phase, such as in the case of SAIB/MIGLYOL® mixtures that are emulsified in water or glycerol, or they may contain the HVLCM as a component of the continuous phase, such as in the case of an aqueous solution that is emulsified in the HVLCM or a solution of the HVLCM in a water immiscible solvent.

Any of the above-described non-polymeric controlled delivery systems can be formulated as liquid, spray, cream, lotion, ointment, gel, slurry, oil, emulsion, microemulsion, solid, plaster, film, particle, microparticle, powder or other suitable form pharmaceutical compositions, suitable for use in the methods of the present invention. In such compositions, the anesthetic agent (e.g., the first anesthetic agent) is included in an amount sufficient to deliver to the subject to be treated an effective amount to achieve a desired effect. The amount of anesthetic agent incorporated into the composition depends upon the final desired release duration and profile, and the concentration of anesthetic required for the intended effect.

The concentration of the anesthetic in the composition will also depend on absorption, inactivation, and excretion rates of that particular agent, as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The composition may be administered in one dosage, or may be divided into a number of smaller doses to be administered at varying intervals of time, either sequentially or concurrently.

The anesthetic agent or agents will typically be present in the composition in the range from about 0.1 to about 99.5 percent by weight relative to the total weight of the composition (wt %), from about 0.5 to about 70 wt %, or from about 1 percent to about 50 wt %. However, ranges having upper endpoints as low as about 40%, 30%, 20%, or 10% can be used, as can ranges having lower limits as high as about 5%, 3%, or 2%. For very active anesthetic agents, the ranges may be less than 1% by weight, and possibly less than 0.0001%.

Both soluble and insoluble anesthetic agents can be distributed using the non-polymeric carrier materials for controlled delivery. Moreover, the compositions may be further formulated with polymeric excipients to provide a delivery matrix with modified properties, for example a faster or slower degradation rate. The resulting composition may be formed into microspheres, or into a macroscopic implant, or other geometries and sizes according to techniques known in the art. Alternatively, a pre-formed microsphere, implant, or polymer particle with the anesthetic agent or agents incorporated therein can be combined with the non-polymeric carrier.

Microspheres may be prepared by a number of methods known in the art, as well as methods described in U.S. Pat. Nos. 6,291,013 and 6,440,493. The polymer particle may be formed using melt extrusion, granulation, solvent mixing, absorption, or like techniques, or the anesthetic agent may be adsorbed onto a polymer matrix, such as an ion exchange resin. The resulting material, when combined suitable non-polymeric carrier material may be administered parenterally. In other embodiments, the anesthetic agent may be combined with a non-polymeric material, such as calcium phosphate or sucrose, to provide layering/barrier properties that lengthen degradation. The non-polymeric carrier will then form a secondary barrier to provide enhanced delivery characteristics. The non-polymeric carrier phase may or may not contain other biologically active substances, according to the specific requirement of the selected application. These other biologically active agents may be any suitable therapeutic and/or prophylactic pharmaceutical, provided that the added substance is suitable for incorporation into microspheres or implants according to techniques known in the art.

As discussed above, a variety of additives can optionally be added to the compositions of the present invention to modify the properties thereof, and in particular to modify the release properties of the composition with respect to the anesthetic agents contained therein. The additives can be present in any amount sufficient to impart the desired properties to the composition. The amount of additive used will in general be a function of the nature of the additive and the effect to be achieved, and can be easily determined by the routineer. Suitable additives are described in U.S. Pat. No. 5,747,058, the entire contents of which are hereby incorporated by reference. More particularly, suitable additives include water, biodegradable polymers, non-biodegradable polymers, natural oils, synthetic oils, carbohydrates or carbohydrate derivatives, inorganic salts, BSA (bovine serum albumin), surfactants, organic compounds, such as sugars, and organic salts, such as sodium citrate. In general, the less water soluble, i.e., the more lipophilic, the additive, the more it will decrease the rate of release of the anesthetic agent, compared to the same composition without the additive. In addition, it may be desirable to include additives that increase properties such as the strength or the porosity of the composition.

The addition of additives can also be used to lengthen the delivery time for the anesthetic agent, making the composition suitable for medical applications requiring or responsive to longer-term administration. Suitable additives in this regard include those disclosed in U.S. Pat. Nos. 5,747,058 and 5,736,152. In particular, suitable additives for this purpose include polymeric additives, such as cellulosic polymers and biodegradable polymers. Suitable cellulosic polymers include cellulose acetates, cellulose ethers, and cellulose acetate butyrates. Suitable biodegradable polymers include polylactones, polyanhydrides, and polyorthoesters, in particular, polylactic acid, polyglycolic acid, polycaprolactone, and copolymers thereof.

When present, the additive is typically present in the compositions in an amount in the range from about 0.01 percent to about 20 percent by weight, more particularly from about 0.1 percent to about 20 percent by weight, relative to the total weight of the composition, and more typically, is present in the composition in an amount in the range from about 1, 2, or 5 percent to about 10 percent by weight. Certain additives, such as buffers, are only present in small amounts in the composition.

The following categories are nonlimiting examples of classes of additives that can be employed in the compositions of the present invention.

One category of additives are biodegradable polymers and oligomers. The polymers can be used to alter the release profile of the anesthetic agent to be delivered, to add integrity to the composition, or to otherwise modify the properties of the composition. Non-limiting examples of suitable biodegradable polymers and oligomers include: poly(lactide), poly(lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly(malic acid), chitin, chitosan, and copolymers, terpolymers, oxidized cellulose, or combinations or mixtures of the above materials.

Examples of poly($\alpha$-hydroxy acid)s include poly(glycolic acid), poly(DL-lactic acid) and poly(L-lactic acid), and their copolymers. Examples of polylactones include poly($\epsilon$-caprolactone), poly($\delta$-valerolactone) and poly($\gamma$-butyrolactone).

While not wishing to be bound by any theory, it is believed that when the composition contains a biodegradeable polymer, a portion of the polymer may precipitate or coagulate at the surface of the composition as any included solvent diffuses away from the material after administration to the subject. The polymer may thus be added as a release modifying agent to affect the release of the anesthetic agent or agents, or may be added as part of a composition containing pre-formed microspheres, implants, or ground polymer particles. The precipitation or coagulation of the polymer forms a skin at least partially surrounding the liquid core of such composition. This skin is porous, and allows the solvent to continue to diffuse through it into surrounding tissue. The rate of solvent release and the extent of formation of the skin, as well as its porosity, can be controlled by the amount and type of solvent and polymer used in the composition.

Other additives for use with the present compositions are non-biodegradable polymers. Non-limiting examples of non-erodible polymers which can be used as additives include: polyacrylates, ethylene-vinyl acetate polymers, cellulose and cellulose derivatives, acyl substituted cellulose acetates and derivatives thereof, non-erodible polyurethanes, polystyrenes, polyvinyl chloride, polyvinyl fluoride, polyvinyl (imidazole), chlorosulphonated polyolefins, polyethylene oxide, and polyethylene.

Preferred non-biodegradable polymers include polyvinyl pyrrolidone, ethylene vinylacetate, polyethylene glycol, cellulose acetate butyrate ("CAB") and cellulose acetate propionate ("CAP").

A further class of additives which can be used in the present compositions are natural and synthetic oils and fats. Oils derived from animals or from plant seeds of nuts typically include glycerides of the fatty acids, chiefly oleic, palmitic, stearic, and linoleic. As a rule the more hydrogen the molecule contains the thicker the oil becomes.

Non-limiting examples of suitable natural and synthetic oils include vegetable oil, peanut oil, medium chain triglycerides, soybean oil, almond oil, olive oil, sesame oil, fennel oil, camellia oil, corn oil, castor oil, cotton seed oil, and soybean oil, either crude or refined, and medium chain fatty acid triglycerides.

Fats are typically glyceryl esters of higher fatty acids such as stearic and palmitic. Such esters and their mixtures are solids at room temperatures and exhibit crystalline structure. Lard and tallow are examples. In general oils and fats increase the hydrophobicity of a non-polymeric carrier system, slowing degradation and water uptake.

All of the above-described compositions may be used in the methods of the present invention in order to provide sustained local anesthesia at a target site. In particular, the compositions may be formulated as liquid, spray, cream, lotion, ointment, gel, slurry, oil, emulsion, microemulsion, solid, plaster, film, particle, microparticle, powder or any other suitable pharmaceutical composition form and then administered to a subject via topical, transdermal, parenteral (e.g., injection, implant, etc.) or like delivery techniques. The compositions, containing an anesthetic and a pharmaceutically acceptable non-polymeric carrier, are used to provide an anesthetic effect characterized by sustained local anesthesia after administration to the subject without an initial burst and a duration of at least about 24 hours after administration, preferably at least about 36 to 48 hours after administration, and more preferably at least about 48 to 72 hours after administration. In certain embodiments, the onset of the local anesthesia occurs within about 2 hours of administration to the subject, preferably within about 1 hour of administration, and in some cases within about 30 minutes of administration to the subject.

The term "subject," as used herein, refers to any vertebrate in which it is desired to provide a state of local anesthesia. The term thus broadly refers to any animal that is to be treated with the compositions of the present invention, such as birds, fish and mammals including humans. In certain embodiments, the methods of the present invention are suitable to provide sustained anesthesia in veterinary practice and animal husbandry, e.g., birds and mammals, whenever a long-term state of local anesthesia is convenient or desirable. In certain cases, the compositions are particularly suited for used with companion animals such as dogs or cats, and additionally may be used with horses. In preferred embodiments, the term "subject" intends a human subject. Furthermore, the term "subject" does not denote a particular age, and the compositions are thus suited for use with subjects of any age, such as infant, adolescent, adult and senior aged subjects.

In preferred embodiments, the compositions of the present invention are particularly suited for use in the treatment of wounds. The non-polymeric carrier systems allow the anesthetic agent or agents to be easily applied to the wound, either directly within the wound and/or adjacent to the wound, using very simple application techniques such dropping on, spraying, painting, spreading, molding or otherwise manually manipulating a liquid, spray, cream, lotion, ointment, gel, slurry, oil, emulsion, microemulsion, pliable solid or plaster, film, particle, microparticle, or powder composition into the wound. The compositions can thus be used with any sized or shaped wound, and will provide an even distribution of the anesthetic agent or agents over the entire area of the wound for better retention and efficacy. Wounds that can be treated using such methods my range for the most superficial to deep, from surface to incisional and from surgical (or otherwise deliberate) to accidental. If the composition is to be injected, it may be applied to the subcutaneous space using a trailing injection alongside the wound on all sides or outside boundaries. Combination approaches may also be employed, such as where the composition is both laid directly into the wound, e.g., prior to surgical closure of the sound, and additionally along the wound. In a particularly preferred embodiment, the methods of the invention involve the use of the instant compositions as a local anesthetic for treatment of post-operative incisional pain. Use of the present compositions in this manner may obviate or at least mitigate the necessity to provide adjunct therapies, such as the administration of systemic narcotic analgesics in order to treat such post-operative pain. Accordingly, the compositions may be used to treat post-operative pain that accompanies all types of medical procedures, such as major surgeries (e.g. thoracotomy, aortic repair, bowel resection), intermediate surgeries (e.g., cesarean section, hysterectomy and appendectomy), and minor surgeries (laparoscopy, arthroscopy, and biopsy procedures), that can otherwise be debilitating and may require pain treatment for 3 to 5 days after surgery.

The compositions described herein can thus be administered in the practice of the instant methods using a wide variety of methods. For example, the compositions may be administered topically, systematically (for example, mucosally (orally, rectally, vaginally, or nasally), parenterally (intravenously, subcutaneously, intramuscularly, or intraperitoneally), or the like. The compositions may be applied via injection, pouring, spray dip, aerosol, or coating applicator. Aerosols or mists of the composition can be administered using an aerosol propellant, e.g., for topical administration, or using a suitable nebulizer, e.g., for nasal, or oral mucosal administration.

Preferably, the compositions are administered as liquids via injection, or in an aerosol, paste or emulsion. When used in an aerosol, any solvent present in the aerosol solution will typically evaporate upon application, allowing the composition to set-up as a film. Alternatively, the aerosol or emulsion may be prepared without a solvent. In this situation, the aerosol propellant can also function as a solvent. Formation of aerosols and emulsions can be accomplished using techniques known to those skilled in the art. See, for example, Ansel, H. C. et al., *Pharmaceutical Dosage Forms and Drug Delivery Systems*, Sixth Edition (1995).

In addition to the uses described above, the present compositions can be administered through osmotic pumps. In one embodiment, a device is designed to be implanted in the tissue of the subject, and designed to effect sustained release over time.

It is also possible to administer the compositions of the invention using a porous or nonporous tube, desirably made of extruded biodegradeable polymer. The tube may be prepared with varying degrees of porosity depending on the characteristics of the composition and the release characteristics desired. The composition of the invention is inserted into the tube, and the ends of the tube may be left open, allowing biologically active compound to diffuse out of the ends of the tube, or may be closed off with additional porous or nonporous polymer. Porous endcaps and porous tubes allow active compound to diffuse through the pores over time. Nonporous endcaps, as well as nonporous tubes, allow anesthetic agents that are soluble in the polymer to diffuse through it and into surrounding tissues. Nonporous materials that are not solvents for the anesthetic, but that are biodegradable, will release the anesthetic when they degrade sufficiently. The compositions of the invention may be prepared and stored as multi-component systems until ready for administration. The number of different components will depend, in part, on the characteristics of the composition. Prior to administration, the components are combined and mixed, e.g., to achieve a homogeneous composition, which can then be administered to the subject. Solvents or additives may be added to one or all of the components, or may form a separate component, which is also mixed with the others prior to administration. Separation of the composition into a multicomponent mixture allows the storage conditions for each component to be optimized, and minimizes any detrimental interactions between components over time. The result is increased storage stability.

EXAMPLES

Below are examples of specific embodiments for carrying out the present invention. The examples are offered for illustrative purposes only, and are not intended to limit the scope of the present invention in any way.

General Methods

The in-vivo efficacy of the compositions and methods of the invention may be assessed in the rat using a hotplate model, e.g., according to the procedure described in detail in IACUC No 9511-2199. The efficacy criteria established for compositions of the invention are mean latency greater than about 2 seconds, with a 12 second cut-off (this cutoff is imposed to prevent any possible damage to the animal). Latencies at 2 seconds are demonstrative of a statistically significant effect of the local anesthetic. Preferably, the mean latency under the rat hotplate model is greater than 7 seconds. Preferably, the percent responders is 50% or greater. Preferably, the compositions of the invention provide a mean latency under the rat hotplate model greater than about 7 seconds to about 12 seconds, with the percent of rats exhibiting the effect being at least about 50% of those tested.

The rat hotplate methodology is summarized as follows. Male Sprague Dawley rats (Harlan Laboratories, Indianapolis, Ind.) with an average weight of 275 gm are used. The hotplate study consists of gently holding the body of the animal while the plantar surface of the hind paw is placed on a hotplate heated to 56° C. Baseline latency is determined prior to unilateral injection of anesthetic composition around the sciatic nerve of the rat.

Sensory testing in human models is also useful in the testing of the compositions of the present invention. The local anesthetic activity can be examined with reference to onset, peak density and duration of effect using seven specific modalities: (a) mechanical sensory testing (mechanical pain detection threshold using von Frey hairs; (b) suprathreshold (mechanical) testing using a single von Frey hair; (c) thermal sensory testing (warm detection threshold); (d) heat pain detection threshold; (e) suprathreshold (heat) testing; (f) cool detection threshold; and (g) tactile sensory testing (mechanical touch detection threshold). The varying degrees or levels of the results will be indicative of the subject experiencing local pain relief, local numbness, and or local nerve blockade. The anesthetic activity of the compositions and methods of the invention can be further characterized with respect to safety, by various measures of activity such as systemic blood plasma levels attained after administration at the localized site.

Mechanical pain detection threshold is defined as the lowest force or number of a von Frey Hair which produces a definite sensation of pain or discomfort, and Mechanical touch detection threshold is defined as the lowest force or number of a von Frey Hair which produces a sensation of touch or pressure. Mechanical Touch Detection Threshold and Mechanical Pain Detection Thresholds can be determined simultaneously using progressively rigid von Frey Hairs (VFH) (available from Somedic A/B, Stockholm, Sweden). It ha previously been determined that each VFH pressed against a balance until it slightly flexed represents a force which logarithmically increases with each hair, covering a total range of 3 to 402 milliNewtons (mN) (VFH No. 7=3 mN; VFH No. 8=13 mN; VFH No. 9=20 mN; VFH No. 10=39 mN; VFH No. 11=59 mN; VFH No. 12=98 mN; VFH No. 13=128 mN; VFH No. 14=133 mN; VFH No. 15=314 mN; VFH No. 16=350 mN; VFH No. 17=402 mN).

Accordingly, in a human subject, an area injected with a composition produced according to the present invention can be stimulated 8 times with each VFH at a rate of about 2 stimuli per second, starting with VFH No. 7 and moving to VFH No. 17. The lowest VFH number that is sensed as touch or pressure (Mechanical Touch Detection Threshold) and the lowest number of the hair in which half of the eight stimulations are painful or unpleasant (Mechanical Pain Detection Threshold) are recorded. The procedure is repeated two more times and the median of the three measurements is reported. If VFH No. 17 does not produce the sensation of touch or pressure a Mechanical Touch Detection Threshold value of 18 will be assigned. If VFH No. 17 does not produce any pain or discomfort a Mechanical Pain Detection Threshold value of 18 will be assigned. Suprathreshold Pain Response-Mechanical to a single von Frey Hair is determined by stimulating the injected areas five times with VFH No. 17 (402 mN). The subject assesses the pain using a VRS scale of 0-10, where zero (0)=no pain, and ten=(10) pain as intense as imaginable.

As discussed above, this test is conducted with a single rigid von Frey Hair that is determined to produce a painful response in subjects. Pain response is determined by stimulating an injected or otherwise treated area 5 times with VFH No. 17. Subjects rate pain on the Verbal Rank Scale (VRS) of 0 to 10, as above.

Thermal testing (Suprathreshold Pain Response-Heat) in a treated area is determined by a stimulus of 45° C., lasting 5 seconds using a computerized thermode (available from Thermostest, Somedic A/B, Stockholm, Sweden) on treated areas. The subject assesses pain on a Verbal Rank Scale (VRS) of 0-10.

Warm Detection Threshold is defined as the lowest increase in temperature from 32° C. perceived, Heat pain Detection Threshold is defined as the lowest temperature perceived as painful, and Cool Detection Threshold is defined as the lowest decrease in temperature from 32° C. perceived. Warm Detection Threshold, Heat Pain Detection Threshold and Cool Detection Threshold are determined with a computerized Thermostest (available from Somedic A/B, Stockholm, Sweden) in treated areas. Subjects are instructed to press a button as soon as the specified sensation is reached. Thermal thresholds are determined from a baseline of 32° C. and increased (Warm Detection Threshold and Heat Pain Detection Threshold) or decreased (Cool Detection Threshold) at a rate of change of 1° C. per second. The upper cut off limit is 52° C. for Warm Detection Threshold and Heat Pain Detection Threshold. The lower cut off limit is 25° C. for Cool Detection Threshold.

Warm Detection Threshold, Heat Pain Detection Threshold and Cool Detection Threshold are calculated as the median of three measurements, with intervals of 10 seconds between each stimulus. If the subject has not perceived warmth or pain at 52° C., the value 53° C. is recorded for Warm Detection Threshold; if the subject has not perceived pain by 52° C., the value of 53° C. is recorded for Heat Pain Detection Threshold; and if the subject has not perceived coolness or pain at 25° C., the value 24° C. is recorded for Cool Detection Threshold.

Example 1

A non-polymeric liquid carrier system containing an anesthetic agent was produced as follows. Sucrose acetate isobutyrate (SAIB) was combined with a N-methylpyrrolidone (NMP) solvent for the SAIB carrier to provide a 70:30 mixture. To this mixture either 2.5% (w/v) or 5% bupivacaine (free base) was added to provide two test compositions.

Male Sprague Dawley Rats, (275 to 300 g) were split into two test groups of 8 animals each. The test formulations were administered into the quadrupeds using needle and syringe to deliver either 25 or 50 mg doses of the bupivacaine. The skin flinch response test was then used to determine the presence of a local anesthetic effect, wherein involuntary flinch upon cutaneous stimulation using a pin applied to 10 random areas within 1 cm of the base of the injection site. Percent inhibition of pin-perception was then calculated by taking the baseline response minus the test response, divided by the baseline response and multiplied by 100.

The results obtained indicated that both test compositions provided local anesthetic effect for up to about 60-72 hours duration, with an onset of activity within 1 hour of administration.

Example 2

Subjects. Male, Fisher 344 rats (Charles River Laboratories) (N=96) were used for the study. Animals were kept on a reversed light:dark cycle (dark 5:00 to 17:00) in a temperature and humidity controlled vivarium. Rats were given ad lib access to food and water except during experimental sessions. All experiments were conducted during the dark phase of the light:dark cycle. All procedures were approved by the Institutional Animal Care and Use Committee of Wake Forest University Health Sciences Center.

Surgical procedure. Following induction of anesthesia with 5% isoflurane vapor in oxygen, animals were shaved on the left lower quadrant of the abdomen. Anesthesia was maintained throughout the surgical procedure using 2.0 to 2.5% isoflurane vapor in oxygen. A 3 cm incision was placed 0.5 cm below and parallel to the lowest rib on the left side, penetrating into the peritoneal cavity. The viscera and musculature were vigorously manipulated by inserting 5 to 7 cm of the index finger into the peritoneal cavity and stretching the musculature. Approximately 10 cm of the small intestine was exteriorized and gently manipulated. The intestine was placed inside the peritoneal cavity and the wound was sutured in 3 layers consisting of the peritoneal lining, abdominal muscles and skin using 4.0 chromic gut. Exterior wounds were dressed with antibiotic powder (Polysporin®, Glaxo-Wellcome, Research Triangle Park, N.C.) and animals were given 75,000 U of penicillin G procaine i.m. Sham-treated animals were anesthetized, shaved, maintained under isoflurane anesthesia for 20 min and given penicillin G procaine i.m.

Administration of the controlled release bupivacaine composition. Test animals were administered either vehicle (70:30, SAIB:NMP), 1.25% (w/v), 2.5% or 5% bupivicaine according to table 1. The composition was administered following suturing of the skin using a trailing injection technique with a 1.0 ml syringe and a 1.5 in 22 ga needle such that 0.25 ml of the composition was evenly distributed over the incision area at approximately 0.5 cm above the wound site. A second administration was given in a similar manner 0.5 cm below the wound site. For groups K and L, an additional administration of 0.1 ml of either 1.25% (w/v) or 5% bupivicaine was given on top of the peritoneal lining using the trailing injection technique prior to suturing the outer muscle layer. The bupivicaine composition was allowed to remain on the peritoneal lining for 1 to 2 min prior to suturing the outer muscle to achieve sufficient viscosity and thereby prevent the composition from leaching through the outer muscle during the suturing process.

TABLE 1

Groups were treated as described below. All groups, with the exception of group B, received surgical laparotomy as described above.

| Group | Treatment |
|---|---|
| AA | No treatment |
| BB | Sham surgery |
| CC | 0.5 ml Vehicle |
| DD | 0.5 ml 1.25% bupivicaine |
| EE | 0.5 ml 2.5% bupivicaine |
| FF | 0.5 ml 5% bupivicaine |
| GG | 0.1 ml inner, 0.5 ml outer 1.25% bupivicaine |
| HH | 0.1 ml inner, 0.5 ml outer 5% bupivicaine |

Measurement of Spontaneous Locomotion. Exploratory behavior was assessed beginning 24 hr after laparotomy using commercially available equipment and software (Med Associates Inc., St. Albans, Vt.). Activity chambers consisted of acrylic enclosures measuring 17"×17" that were 15" tall with an open top. Duplicate banks of 16 infrared transmitters spaced 1" apart were placed in both the X and Y directions, 1" above the floor surface, with aligned infrared detectors on the opposing sides of the chamber. A third bank of infrared transmitters and detectors was located in the X direction, 7 cm above the floor surface such that the rats used for these studies was required to rear on its hind limbs in order to interrupt these beams. Each activity chamber was housed within a light- and sound-attenuating enclosure. Sessions were conducted at 16, 24, 40, 48 and 72 hours post-operative and were 60 min in duration. Measures collected include total distance traveled, total beam breaks in both the X and Y direction (ambulatory counts), repeated beam breaks within 3 cm of the animal in the absence of locomotion (stereotypy), total beam breaks in the upper X direction (rearing), time spent in ambulation, time spent in stereotypy, time spent rearing and time spent at rest. All measures were collected in 6 min bins throughout the session as well as summed for the entirety of the session.

Measurement of return of aesthesia using pin prick test. At 96 hours post-operative, animals were lightly restrained in a clear acrylic holding chamber that allows access to the abdominal area. A slightly blunted 20 ga needle was pushed into a region within 0.5 cm of the abdominal wound site with sufficient force to noticeably involute the abdominal tissue. The needle was kept in place for 10 seconds or until the animal reacted by flinching or pulling away from the needle. Each animal was tested 2 to 3 times at the wound site. A site at least 10 cm away from the wound area was tested in a similar manner as a positive control measure.

Data analysis. Data were analyzed using a 2-factor ANOVA for repeated measures with individual behavioral indices serving as the independent measure and both treatment group and post-operative time as the dependent variables. Post-hoc analyses were performed using Bonferroni-Dunn t-test for multiple comparisons with the sham surgery group serving as control and using Fisher's Protected LSD for all pair wise comparisons.

Results (distance traveled). The effects of surgery and perioperative treatment with either vehicle or bupivicaine are shown for each time point in FIGS. 1-5. There was a significant main effect of treatment group and time after surgery on distance traveled with no significant interaction between these variables (Table 1).

TABLE 2

2-Factor ANOVA results for distance traveled (cm).

| Source | df | Sum of Squares | Mean Square | F-Value | P-Value |
|---|---|---|---|---|---|
| group | 7 | 26500237.696 | 3.78575E6 | 2.2594 | .0288 |
| time | 4 | 3.37791E7 | 8.44478E6 | 5.0401 | .0006 |
| group * time | 28 | 6.07196E7 | 2.16856E6 | 1.2943 | .1468 |
| Residual | 435 | 7.28855E8 | 1.67553E6 | | |

Dependent: distance

Post-hoc analysis using the Bonferroni/Dunn t-test for multiple comparisons to a control group revealed that all groups administered bupivicaine were not significantly different from sham treatment, whereas incision animals given no treatment or vehicle treated animals remained significantly different from sham controls throughout the study (Table 2). Post-hoc analysis of all pair wise comparisons using Fisher's Protected LSD found that only the groups administered 5% bupivicaine or 1.25% bupivicaine both at the site of the peritoneal lining and at the outer muscle were not significantly different from sham (Table 3).

TABLE 3

Fisher's Protected LSD for all pair wise comparisons, distance traveled (cm).

| | Vs. | Diff. | Crit. diff. | P-Value | |
|---|---|---|---|---|---|
| vehicle | incision | 116.35748 | 474.92594 | .6304 | |
| | 1.25% saber | 213.04748 | 474.92594 | .3784 | |
| | layered in/out 5% | 332.81365 | 474.92594 | .1691 | |
| | 2.5% saber | 343.37232 | 474.92594 | .1560 | |
| | both in/out 1.25% | 402.70898 | 474.92594 | .0963 | |
| | 5% saber | 514.73865 | 474.92594 | .0337 | S |
| | sham | 825.22848 | 474.92594 | .0007 | S |
| incision | 1.25% saber | 96.69000 | 464.48674 | .6826 | |
| | layered in/out 5% | 216.45617 | 464.48674 | .3602 | |
| | 2.5% saber | 227.01483 | 464.48674 | .3373 | |
| | both in/out 1.25% | 286.35150 | 464.48674 | .2263 | |
| | 5% saber | 398.38117 | 464.48674 | .0926 | |
| | sham | 708.87100 | 464.48674 | .0029 | S |
| 1.25% saber | layered in/out 5% | 119.76617 | 464.48674 | .6126 | |
| | 2.5% saber | 130.32483 | 464.48674 | .5816 | |
| | both in/out 1.25% | 189.66150 | 464.48674 | .4227 | |
| | 5% saber | 301.69117 | 464.48674 | .2024 | |
| | sham | 612.18100 | 464.48674 | .0099 | S |
| layered in/out 5% | 2.5% saber | 10.55867 | 464.48674 | .9644 | |
| | both in/out 1.25% | 69.89533 | 464.48674 | .7676 | |
| | 5% saber | 181.92500 | 464.48674 | .4418 | |
| | sham | 492.41483 | 464.48674 | .0378 | S |
| 2.5% saber | both in/out 1.25% | 59.33667 | 464.48674 | .8019 | |
| | 5% saber | 171.36633 | 464.48674 | .4688 | |
| | sham | 481.85617 | 464.48674 | .0421 | S |
| both in/out 1.25% | 5% saber | 112.02967 | 464.48674 | .6357 | |
| | sham | 422.51950 | 464.48674 | .0745 | |
| 5% saber | sham | 310.48983 | 464.48674 | .1896 | |

S = Significantly different at this level.

Ambulatory counts. The statistical results for ambulatory count data is qualitatively similar to those described for distance traveled above. The data for ambulatory counts were assessed for each individual time point following surgery. As with distance traveled during the session, there was a significant main effect of both treatment group and time after surgery on ambulatory counts, with no significant interaction between these variables (Table 4).

TABLE 4

2-Factor ANOVA results for ambulatory counts.

| Source | df | Sum of Squares | Mean Square | F-Value | P-Value |
|---|---|---|---|---|---|
| group | 7 | 5.70066E6 | 8.1438E5 | 1.9317 | .0631 |
| time | 4 | 8.44878E6 | 2.1122E6 | 5.0101 | .0006 |
| group * time | 28 | 1.42666E7 | 5.09522E5 | 1.2086 | .2161 |
| Residual | 435 | 1.83392E8 | 4.21591E5 | | |

Dependent: ambulatory counts

Post-hoc analysis with the Bonferroni/Dunn t-test using ambulatory counts as the independent measure yielded similar results as the data for distance traveled (Tables 5).

TABLE 5

Bonferroni/Dunn t-test for multiple comparisons, ambulatory counts.

| | Vs. | Diff. | Crit. diff. | P-Value | |
|---|---|---|---|---|---|
| sham | incision | −354.50000 | 325.73352 | .0029 | S |
| | vehicle | −346.51061 | 333.05428 | .0045 | S |
| | 1.25% saber | −281.00000 | 325.73352 | .0182 | |
| | layered in/out 5% | −213.43333 | 325.73352 | .0725 | |
| | 2.5% saber | −207.28333 | 325.73352 | .0811 | |
| | both in/out 1.25% | −174.08333 | 325.73352 | .1427 | |
| | 5% saber | −128.61667 | 325.73352 | .2785 | |

S = Significantly different at this level.

Analysis of all pair wise comparisons with Fisher's Protected LSD found that the sham group was only significantly different from the control incision group, the vehicle-treated group and the group treated with the lowest dose of bupivicaine (1.25%) (Table 6).

TABLE 6

Fisher's Protected LSD for all pair wise comparisons, ambulatory counts.

| | Vs. | Diff. | Crit. diff. | P-Value | |
|---|---|---|---|---|---|
| incision | vehicle | 7.98939 | 238.22966 | .9475 | |
| | 1.25% saber | 73.50000 | 232.99321 | .5356 | |
| | layered in/out 5% | 141.06667 | 232.99321 | .2347 | |
| | 2.5% saber | 147.21667 | 232.99321 | .2150 | |
| | both in/out 1.25% | 180.41667 | 232.99321 | .1288 | |
| | 5% saber | 225.88333 | 232.99321 | .0574 | |
| | sham | 354.50000 | 232.99321 | .0029 | S |
| vehicle | 1.25% saber | 65.51061 | 238.22966 | .5891 | |
| | layered in/out 5% | 133.07727 | 238.22966 | .2729 | |
| | 2.5% saber | 139.22727 | 238.22966 | .2513 | |
| | both in/out 1.25% | 172.42727 | 238.22966 | .1556 | |
| | 5% saber | 217.89394 | 238.22966 | .0729 | |
| | sham | 346.51061 | 238.22966 | .0045 | S |
| 1.25% saber | layered in/out 5% | 67.56667 | 232.99321 | .5690 | |
| | 2.5% saber | 73.71667 | 232.99321 | .5344 | |
| | both in/out 1.25% | 106.91667 | 232.99321 | .3676 | |
| | 5% saber | 152.38333 | 232.99321 | .1993 | |
| | sham | 281.00000 | 232.99321 | .0182 | S |
| layered in/out 5% | 2.5% saber | 6.15000 | 232.99321 | .9586 | |
| | both in/out 1.25% | 39.35000 | 232.99321 | .7401 | |
| | 5% saber | 84.81667 | 232.99321 | .4747 | |
| | sham | 213.43333 | 232.99321 | .0725 | |
| 2.5% saber | both in/out 1.25% | 33.20000 | 232.99321 | .7796 | |
| | 5% saber | 78.66667 | 232.99321 | .5073 | |
| | sham | 207.28333 | 232.99321 | .0811 | |
| both in/out 1.25% | 5% saber | 45.46667 | 232.99321 | .7015 | |
| | sham | 174.08333 | 232.99321 | .1427 | |
| 5% saber | sham | 128.61667 | 232.99321 | .2785 | |

S = Significantly different at this level.

Stereotypy Counts. There were no significant differences found between groups for close movements (stereotypy) but there was a significant main effect of time after surgery and a significant interaction between treatment group and post-surgical time (Table 7, FIGS. 11-15). Post-hoc analysis using Bonferroni/Dunn t-test revealed that the 40 hr time point was significantly different from the other time points for this measure (Table 8). Exclusion of the 40 hr time point and reanalysis of the remaining data by 2-factor ANOVA revealed a marginally significant effect of treatment group on stereotypic behavior, a significant main effect of post-surgical time and a significant interaction between treatment group and time after surgery (Table 9). Post-hoc analysis by Bonferroni/Dunn revealed no significant differences between treatment groups, but Fisher's Protected LSD t-test found that all groups were significantly different from sham controls with the exception of the highest dose of bupivicaine (5%) as well as the group treated with 1.25% bupivicaine both at the level of the peritoneal lining and at the abdominal muscle layer (Table 10).

TABLE 7

2-Factor ANOVA, stereotypy counts.

| Source | df | Sum of Squares | Mean Square | F-Value | P-Value |
|---|---|---|---|---|---|
| group | 7 | 8.17653E6 | 1.16808E6 | 1.2165 | .2921 |
| time | 4 | 2.00711E7 | 5.01778E6 | 5.2258 | .0004 |
| group * time | 28 | 4.64266E7 | 1.65809E6 | 1.7268 | .0131 |
| Residual | 435 | 4.17686E8 | 9.60197E5 | | |

Dependent: stereotypy counts

TABLE 8

Bonferroni/Dunn for multiple comparisons to control, time after surgery.

| | Vs. | Diff. | Crit. diff. | P-Value | |
|---|---|---|---|---|---|
| 16 | 24 | −95.29474 | 367.84078 | .5031 | |
| | 48 | −44.54737 | 367.84078 | .7542 | |
| | 72 | 300.09474 | 367.84078 | .0354 | |
| | 40 | 415.45263 | 367.84078 | .0037 | S |

S = Significantly different at this level.

TABLE 9

2-Factor ANOVA, excluding 40 hr time point, stereotypy counts.

| Source | df | Sum of Squares | Mean Square | F-Value | P-Value |
|---|---|---|---|---|---|
| group | 7 | 1.2537E7 | 1.791E6 | 1.8741 | .0729 |
| time | 3 | 9.26855E6 | 3.08952E6 | 3.2329 | .0225 |
| group * time | 21 | 3.24302E7 | 1.54429E6 | 1.616 | .0435 |
| Residual | 348 | 3.32568E8 | 9.55656E5 | | |

Dependent: stereotypy counts

TABLE 10

Fisher's Protected LSD for all pair wise comparisons excluding 40 hr time point, stereotypy counts.

| | Vs. | Diff. | Crit. diff. | P-Value | |
|---|---|---|---|---|---|
| incision | 1.25% saber | 48.54167 | 392.46977 | .8079 | |
| | 2.5% saber | 70.66667 | 392.46977 | .7235 | |
| | layered in/out 5% | 83.68750 | 392.46977 | .6752 | |
| | vehicle | 122.54924 | 401.29041 | .5485 | |
| | both in/out 1.25% | 144.58333 | 392.46977 | .4692 | |
| | 5% saber | 431.95833 | 392.46977 | .0311 | S |
| | sham | 530.02083 | 392.46977 | .0083 | S |

TABLE 10-continued

Fisher's Protected LSD for all pair wise comparisons excluding 40 hr time point, stereotypy counts.

| | Vs. | Diff. | Crit. diff. | P-Value | |
|---|---|---|---|---|---|
| 1.25% saber | 2.5% saber | 22.12500 | 392.46977 | .9118 | |
| | layered in/out 5% | 35.14583 | 392.46977 | .8603 | |
| | vehicle | 74.00758 | 401.29041 | .7170 | |
| | both in/out 1.25% | 96.04167 | 392.46977 | .6306 | |
| | 5% saber | 383.41667 | 392.46977 | .0555 | |
| | sham | 481.47917 | 392.46977 | .0163 | S |
| 2.5% saber | layered in/out 5% | 13.02083 | 392.46977 | .9480 | |
| | vehicle | 51.88258 | 401.29041 | .7994 | |
| | both in/out 1.25% | 73.91667 | 392.46977 | .7113 | |
| | 5% saber | 361.29167 | 392.46977 | .0711 | |
| | sham | 459.35417 | 392.46977 | .0219 | S |
| layered in/out 5% | vehicle | 38.86174 | 401.29041 | .8491 | |
| | both in/out 1.25% | 60.89583 | 392.46977 | .7604 | |
| | 5% saber | 348.27083 | 392.46977 | .0818 | |
| | sham | 446.33333 | 392.46977 | .0259 | S |
| vehicle | both in/out 1.25% | 22.03409 | 401.29041 | .9141 | |
| | 5% saber | 309.40909 | 401.29041 | .1303 | |
| | sham | 407.47159 | 401.29041 | .0466 | S |
| both in/out 1.25% | 5% saber | 287.37500 | 392.46977 | .1507 | |
| | sham | 385.43750 | 392.46977 | .0542 | |
| 5% saber | sham | 98.06250 | 392.46977 | .6234 | |

S = Significantly different at this level.

Vertical Counts (rearing). There was a significant main effect of both treatment group and time after surgery on rearing, as well as a significant interaction between these variables (Table 11). Post-hoc analysis using the Bonferroni/Dunn t-test revealed significant differences between the sham control and all treatment groups (Table 12). The results of the Fisher's Protected LSD test yielded consistent findings, with no significant differences found with the exception of the sham group with all other treatments (Table 13).

TABLE 11

2-Factor ANOVA, vertical counts.

| Source | df | Sum of Squares | Mean Square | F-Value | P-Value |
|---|---|---|---|---|---|
| group | 7 | 25480.85893 | 3640.12270 | 6.1118 | .0001 |
| time | 4 | 7396.90415 | 1849.22604 | 3.1049 | .0154 |
| group * time | 28 | 30524.37145 | 1090.15612 | 1.8304 | .0067 |
| Residual | 435 | 259082.15909 | 595.59117 | | |

Dependent: vertical counts

TABLE 12

Bonferroni/Dunn for multiple comparisons to control, vertical counts.

| | Vs. | Diff. | Crit. diff. | P-Value | |
|---|---|---|---|---|---|
| sham | 1.25% saber | −25.20000 | 12.24308 | .0001 | S |
| | vehicle | −22.60909 | 12.51824 | .0001 | S |
| | layered in/out 5% | −21.95000 | 12.24308 | .0001 | S |
| | 5% saber | −20.80000 | 12.24308 | .0001 | S |
| | incision | −20.63333 | 12.24308 | .0001 | S |
| | both in/out 1.25% | −19.08333 | 12.24308 | .0001 | S |
| | 2.5% saber | −18.65000 | 12.24308 | .0001 | S |

S = Significantly different at this level.

TABLE 13

Fisher's Protected LSD for all pair wise comparisons, vertical counts.

| | Vs. | Diff. | Crit. diff. | P-Value | |
|---|---|---|---|---|---|
| 1.25% saber | vehicle | 2.59091 | 8.95415 | .5699 | |
| | layered in/out 5% | 3.25000 | 8.75733 | .4661 | |
| | 5% saber | 4.40000 | 8.75733 | .3239 | |
| | incision | 4.56667 | 8.75733 | .3060 | |
| | both in/out 1.25% | 6.11667 | 8.75733 | .1705 | |
| | 2.5% saber | 6.55000 | 8.75733 | .1423 | |
| | sham | 25.20000 | 8.75733 | .0001 | S |
| vehicle | layered in/out 5% | .65909 | 8.95415 | .8850 | |
| | 5% saber | 1.80909 | 8.95415 | .6915 | |
| | incision | 1.97576 | 8.95415 | .6647 | |
| | both in/out 1.25% | 3.52576 | 8.95415 | .4394 | |
| | 2.5% saber | 3.95909 | 8.95415 | .3853 | |
| | sham | 22.60909 | 8.95415 | .0001 | S |
| layered in/out 5% | 5% saber | 1.15000 | 8.75733 | .7965 | |
| | incision | 1.31667 | 8.75733 | .7678 | |
| | both in/out 1.25% | 2.86667 | 8.75733 | .5203 | |
| | 2.5% saber | 3.30000 | 8.75733 | .4593 | |
| | sham | 21.95000 | 8.75733 | .0001 | S |
| 5% saber | incision | .16667 | 8.75733 | .9702 | |
| | both in/out 1.25% | 1.71667 | 8.75733 | .7002 | |
| | 2.5% saber | 2.15000 | 8.75733 | .6297 | |
| | sham | 20.80000 | 8.75733 | .0001 | S |
| incision | both in/out 1.25% | 1.55000 | 8.75733 | .7281 | |
| | 2.5% saber | 1.98333 | 8.75733 | .6565 | |
| | sham | 20.63333 | 8.75733 | .0001 | S |
| both in/out 1.25% | 2.5% saber | .43333 | 8.75733 | .9226 | |
| | sham | 19.08333 | 8.75733 | .0001 | S |
| 2.5% saber | sham | 18.65000 | 8.75733 | .0001 | S |

S = Significantly different at this level.

Pin prick stimulus. Animals were subjected to the pin prick stimulus at an area within 0.5 cm of the incision 96 hr after surgery. All animals responded to this stimulus with the exception of a single animal in group HH (1.25% bupivicaine administered at both the abdominal muscle layer and at the peritoneal lining). This animal responded normally to the pin prick stimulus when it was administered at a site approximately 3 cm from the site of the incision.

Results. Peri-operative treatment with the vehicle used for the sustained-release composition (the control) had no significant effect on activity measures compared to abdominal incision with no other treatment. There was an apparent vehicle effect on stereotypic behavior at some of the later time points. The data consistently support a significant analgesic effect of 5% bupivicaine in the sustained-release composition that appears to be present at the later time points studied. The 5% bupivicaine controlled release composition consistently provided substantial analgesia and reversed the effect of abdominal incision on all behavioral measures with the exception of vertical activity. Some analgesic effects were found following administration of 1.25% bupivicaine at both the level of the peritoneal lining and at the outer abdominal muscle layer, however the effects were not as consistent as those found following administration of 5% bupivicaine at the outer muscle layer only. The effect of 5% bupivicaine is more robust at the 48 and 72 hour time points. The reason(s) for these animals displaying less activity at the earlier time points is(are) not readily apparent as these animals displayed normal feeding and grooming behavior in their home cages and did not appear to be in distress. These data establish that local anesthetic effect sufficient to control pain following surgery using the controlled release compositions of the invention containing a bupivicaine anesthetic.

Example 3

The following dose escalation, safety and pharmacokinetic evaluation was carried out in healthy human volunteer subjects in order to assess the safety/tolerability and preliminary pharmacokinetic performance of controlled release bupivacaine compositions comprising a sucrose acetate isobutyrate non-polymeric carrier.

The compositions were formulated using bupivacaine free base formulated in a sucrose acetate isobutyrate (SAIB) non-polymeric carrier further including N-methyl-2-pyrrolidone (NMP) that acts as a solvent for the bupivacaine and the SAIB carrier. The composition was prepared by combining the SAIB carrier and NMP solvent (70:30 vehicle) with 5 wt % of bupivacaine, to provide individual dosages containing 137.5 mg of the bupivacaine in a 2.5 mL injection volume. The composition was provided as an injectable liquid.

There were two Cohorts in the study. Cohort 1 was comprised of 6 healthy male subjects, aged from 22 to 38. For Cohort 1, all subjects received 2.5 mL total volume injections of the SAIB/NMP/bupivacaine composition (containing 137.5 mg bupivacaine) at a first administration site, administered into the abdominal subcutaneous space as a 5 cm trailing injection; and 2.5 mL placebo injections containing vehicle (SAIB/NMP) only at a second administration site, also administered into the abdominal subcutaneous space as a 5 cm trailing injection. After administrations, the subjects were assessed for up to eight hours to monitor local tissue conditions at the site of administration and plasma samples were collected. Additional plasma samples were taken on Days 1, 2, 3, 4 and 28. All plasma samples were tested for bupivacaine concentration in the blood using standard methods.

Cohort 2 was also comprised of 6 healthy male subjects, aged from 22 to 38. Cohort 2 was split into two subgroups, the first subgroup (n=3) received 5 mL total volume injections of the SAIB/NMP/bupivacaine composition (containing 275 mg bupivacaine), administered into the abdominal subcutaneous space as two 5 cm trailing injections of 2.5 mL each. The second subgroup (n=3) received 2.5 mL total volume placebo injections containing vehicle (SAIB/NMP) only, also administered into the abdominal subcutaneous space as two 5 cm trailing injections of 1.25 mL each. Here again, after administrations, the subjects were assessed for up to eight hours to monitor local tissue conditions at the site of administration and plasma samples were collected. Additional plasma samples were taken on Days 1, 2, 3, 4 and 28.

As a result of the study, it was found that the SAIB carrier and SAIB/NMP/bupivacaine compositions were well tolerated, where the injections did not result in any observable redness, swelling, itching, discoloration, or any other adverse symptom at the injections site, or any unacceptable tissue reaction throughout the duration of the study. In addition, the bupivacaine pharmacokinetic evaluations showed suitable slow (extended) release of the bupivacaine active from the SAIB carrier, releasing the bupivacaine active over a period of 3 to 4 days. These pharmacokinetic results are presented in FIG. 1. As can be seen, the $C_{max}$ plasma bupivacaine concentrations following Cohort 1 (84 ng/mL) and Cohort 2 (174 ng/mL) injections were well below published estimated toxic plasma concentration ranges (about 1 to 4 µg/mL). In addition, a comparison between the Cohort 1 and Cohort 2 curves shows that plasma bupivacaine levels increase in a substantially linear fashion with the dose escalation. Furthermore, assessment of the AUC shows that there was 100% bupivacaine bioavailability.

Example 4

The following dose escalation, pharmacokinetic, pharmacodynamic (efficacy) evaluation is carried out in human patients undergoing surgical inguinal hernia repair procedures in order to assess the efficacy and pharmaceutical performance of controlled release bupivacaine compositions comprising a sucrose acetate isobutyrate non-polymeric carrier and prepared in accordance with the present invention.

The study compares the efficacy of the present SAIB/bupivacaine compositions administered subcutaneously in combination with a saline (placebo) or bupivacaine hydrochloride (Marcain®) wound infiltrate, against a commercially available bupivacaine solution (Marcain®, Bupivacaine Hydrochloride BP, 5.28 mg/mL, equivalent to bupivacaine hydrochloride anhydrous 5 mg/mL) administered subcutaneously and as an infiltrate in open inguinal hernia repair patients.

The test composition was/is formulated using bupivacaine free base formulated in a sucrose acetate isobutyrate (SAIB) non-polymeric carrier further including benzyl alcohol (BA) that acts as a solvent for the bupivacaine and the SAIB carrier. The benzyl alcohol is also an anesthetic agent. The composition was/is prepared by combining about 66 wt % of the SAIB carrier, 22 wt % of the benzyl alcohol solvent/anesthetic, and 12 wt % of bupivacaine, to provide individual dosages containing 159.5 mg bupivacaine in a 1.25 mL injection volume (319 mg in a 2.5 mL total volume). The composition was/is provided as an injectable clear liquid.

The study is designed to include 3 Cohorts with up to 91 patients (6 patients for Cohort 1; 15 patients for Cohort 2; and up to 70 patients for Cohort 3). In particular, Cohort 1 was comprised of 6 healthy male subjects, aged from 23 to 52. For Cohort 1, all patients received 2.5 mL total volume injections of the SAIB/BA/bupivacaine composition (containing 319 mg bupivacaine), administered as two trailing subcutaneous injections along each side of the surgical wound (0.5 mL/cm along a suggested 5 cm total length wound incision) with 10 mL saline infiltrated into the incision wound (including subfascial) prior to wound closure. The trailing injections were administered 0.5 to 1.0 cm away from and parallel to the incision wound margins, and were performed by advancing the needle subcutaneously, parallel to and along the length of the incision, injecting continuously as the needle was withdrawn. Anesthetic/analgesic effect was assessed using Time to First Supplemental Analgesic Medication, and Total Supplemental Analgesic Medication Consumption (over the course of 4 days) tests. Plasma bupivacaine concentration was measured periodically throughout the course of the study, particularly through the first 24 hours to assess the magnitude of early bupivacaine release from the SAIB controlled release composition.

The results of the Time to First Supplemental Analgesic test are reported below in Table 14.

TABLE 14

| Time to First Supplemental Analgesic. | |
|---|---|
| Patient # | Time First Analgesic Taken |
| 1 | 8 hours |
| 2 | 1 hour |
| 3 | 1 hour |
| 4 | 1 hour |
| 5 | 2 hours |
| 6 | 3 hours |
| (Mean) | 2.6 hours |

The results of the Total Supplemental Analgesic Medication Consumption (over the course of 4 days) are reported below in Table 15.

TABLE 15

| Total Supplemental Analgesic Medication Consumption. | | | | |
|---|---|---|---|---|
| Patient # | Day 1 | Day 2 | Day 3 | Day 4 |
| 1 | 2 | 5 | 1 | 1 |
| 2 | 4 | 4 | 3 | 4 |

TABLE 15-continued

Total Supplemental Analgesic Medication Consumption.

| Patient # | Day 1 | Day 2 | Day 3 | Day 4 |
|---|---|---|---|---|
| 3 | 3 | 1 | 1 | 1 |
| 4 | 10 | 5 | 3 | 1 |
| 5 | 2 | 1 | 1 | 1 |
| 6 | 4 | 1 | 2 | 3 |
| (Mean) | 4.16 | 2.8 | 1.8 | 1.8 |

As with the Example 3 study, it was again found that the SAIB/BA/bupivacaine composition was well tolerated, where the injections did not result in any observable redness, swelling, itching, discoloration, or any other adverse symptom at the injections site, or any unacceptable tissue reaction throughout the duration of the study. In addition, the bupivacaine pharmacokinetic evaluations showed extended release of the bupivacaine active from the SAIB carrier, releasing the bupivacaine active over a period of 4 days. The pharmacokinetic results are presented in FIGS. 2 and 3. As can be seen, the SAIB/BA/bupivacaine composition released the bupivacaine active quickly (within about 1 hour of administration) without an initial burst and showed a substantially constant, steady state release over at least the first 3 days of treatment. The observed mean $C_{max}$ was 277 ng/mL±109; the $T_{max}$ was 23 hours±21; and the $C_{ss}$ was 191 ng/mL±13.

Cohort 2 was comprised of 15 healthy male subjects, aged from 26 to 54. Cohort 2 was split into three subgroups, the first subgroup (n=5) received 5.0 mL total volume injections of the SAIB/BA/bupivacaine composition (containing 638 mg bupivacaine), administered as two trailing subcutaneous injections along each side of the surgical wound (0.5 mL/cm along a suggested 5 cm total length incision wound) with 10 mL saline infiltrated into the incision wound (including subfascial) prior to wound closure. The second subgroup (n=5) received 5 mL total volume injections of the SAIB/BA/bupivacaine composition (containing 638 mg bupivacaine), administered as two trailing subcutaneous injections along each side of the surgical wound (0.5 mL/cm along a suggested 5 cm total length incision wound) with 10 mL Marcain® (0.5% Bupivacaine-HCl) infiltrated into the incision wound (including subfascial) prior to wound closure to yield a total of 688 mg bupivacaine administered per patient. The third subgroup (n=5) received 5 mL total volume injections of the Marcain® (0.5% Bupivacaine-HCl) composition administered as two trailing subcutaneous injections along each side of the surgical wound (0.5 mL/cm along a suggested 5 cm total length incision wound) along with 10 mL Marcain® infiltrated into the incision wound (including subfascial) prior to wound closure to yield a total of 75 mg bupivacaine administered per patient.

Anesthetic/analgesic effect was assessed using Time to First Supplemental Analgesic Medication, "at rest" Incision Site Pain Scores, and Total Supplemental Analgesic Medication Consumption (over the course of 4 days) tests. Plasma bupivacaine concentration was measured periodically throughout the course of the study, particularly through the first 24 hours to assess the magnitude of early bupivacaine release from the SAIB controlled release composition.

The results of the Time to First Supplemental Analgesic test, and the Total Supplemental Analgesic Medication Consumption (over the course of 4 days) test for all three subgroups for Cohort 2 are reported below in Table 16.

TABLE 16

Mean Time to First Supplemental Analgesic and Mean Total Supplemental Analgesic Medication Consumption (over the course of 4 days).

| Sub-group | Number of Patients | Treatment | Mean Time to First Supplemental Analgesic (in hours) | Mean Number of Supplemental Analgesic Doses Taken Over 4 Days |
|---|---|---|---|---|
| 1 | n = 5 | SAIB/BA/Bupivacaine and Saline (638 mg total dose) | 60.4* | 2.6 |
| 2 | n = 5 | SAIB/BA/Bupivacaine and Marcain ® (688 mg total dose) | 44.9* | 2.4 |
| 3 | n = 5 | Marcain ® (75 mg total dose) | 2.3 | 11.0 |

(*Three patients in Subgroup 1 and two patients in Subgroup 2 took no supplemental analgesic doses over the entire 4 day period.)

Once again, the SAIB/BA/bupivacaine composition was well tolerated (the subgroup 1 and 2 patients), where the injections did not result in any observable redness, swelling, itching, discoloration, or any other adverse symptom at the injections site, or any unacceptable tissue reaction throughout the duration of the study. In addition, the bupivacaine pharmacokinetic evaluations showed extended release of the bupivacaine active from the SAIB carrier, releasing the bupivacaine active over a period of 4 days. The pharmacokinetic results are presented in FIGS. 4 and 5. As can be seen, the SAIB/BA/bupivacaine composition released the bupivacaine active quickly (within about 1 hour of administration) without an initial burst and showed a substantially constant, steady state release over at least the first 3 days of treatment.

The pharmacodynamics for all three subgroups of Cohort 2 are reported below in Table 17.

TABLE 17

Pharmacodynamics for Cohort 2.

| Sub-group | Number of Patients | Treatment | Cmax (ng/mL) | Tmax (hours) | Css (ng/ml) |
|---|---|---|---|---|---|
| 1 | n = 5 | SAIB/BA/Bupivacaine and Saline (638 mg total dose) | 470 ± 155 | 21 ± 25 | 311 ± 58 |
| 2 | n = 5 | SAIB/BA/Bupivacaine and Marcain ® (688 mg total dose) | 310 ± 60 | 21 ± 25 | 291 ± 40 |
| 3 | n = 5 | Marcain ® (75 mg total dose) | 180 ± 88 | 0.6 ± 0.2 | NA |

As can be seen from the results of the Cohort 2 study, the instant controlled release compositions provide effective local anesthetic effect over the course of at least 4 days after surgery, greatly reducing the need for supplemental analgesic medications. In fact, 50% of the patients receiving the SAIB/BA/Bupivacaine compositions of the present invention (5 out of 10 patients in subgroups 1 and 2) required no supplemental pain medications over the entire 4 day period. Those patients in subgroups 1 and 2 that did require supplemental analgesic medications were still able to await their first additional pain medications for about 2-3 days, showing effective local anesthetic effect over the course of at least 2 days after surgery. In addition, the amount of doses of supplemental analgesic medications in subgroups 1 and 2 were drastically reduced relative to the control (subgroup 3) patients who required on average 11 doses over the 4 day test period as contrasted with 2.4 to 2.6 doses over the same period.

Furthermore, a review of the pharmacokinetic data from Cohort 2 suggests that an efficacious subcutaneous dose of 638-688 mg bupivacaine can be reproducibly administered using the controlled release compositions of the present invention to provide an efficacious steady state plasma concentration of bupivacaine of about 300 ng/mL.

Figure 6:
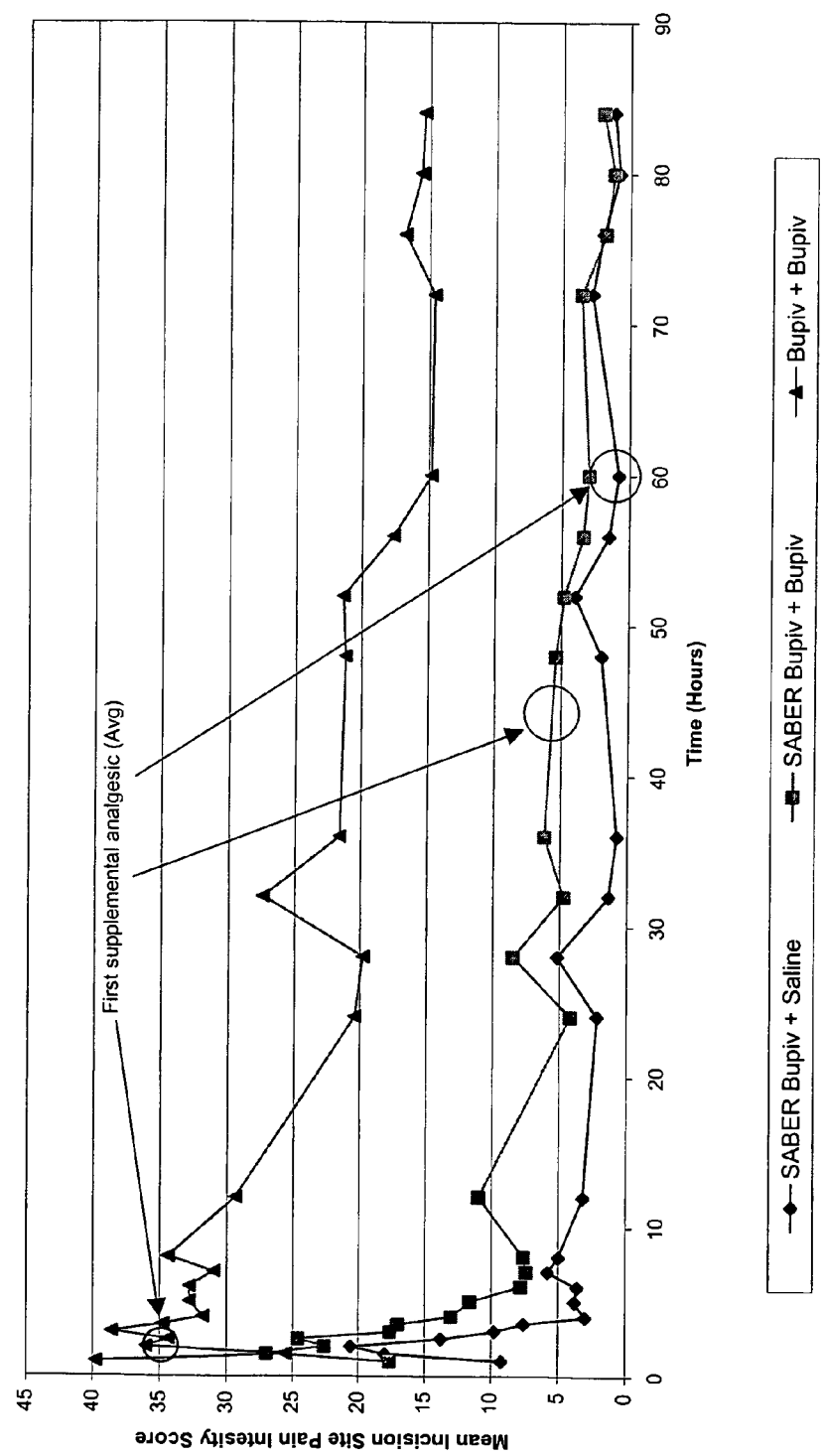
FIG. 6 depicts the mean "at rest" incision site pain scores recorded using a 0 to 100 mm visual analog scale (VAS) from Example 4, Cohort 2, where the subgroup 3 data is represented by the top curve (?), the subgroup 2 data is represented by the middle curve (?), and the subgroup 1 data is represented by the bottom curve (?).

The results of the "at rest" Incision Site Pain Scores test for all three subgroups of Cohort 2 are depicted in FIG. 6. The subgroup 3 data is represented by the top curve (?), the subgroup 2 data is represented by the middle curve (?), and the subgroup 1 data is represented by the bottom curve (?). For convenience, the average time to first supplemental analgesic is shown on each curve. The incision pain intensity was recorded using a 0 to 100 mm visual analog scale (VAS) with scores ranging from 0 (no pain) to 100 (worst pain imaginable). Each VAS score was recorded as a single vertical line on the scale. The test was administered as follows. On the day of surgery (Day 0), incision pain scores were recorded initially at 60 minutes after administration of the test composition (as discussed above, subgroup 1 received SAIB/BA/bupivacaine and saline; subgroup 2 received SAIB/BA/bupivacaine and Marcain®; and subgroup 3 received Marcain® and Marcain®). Thereafter, incision pain scores were recorded every 30 minutes through the 4 hour evaluation time point, and then hourly through the 8 hour evaluation time point, and finally at the 12 hour evaluation time point. On follow-on Days 1 through 3, incision pain scores were recorded in the morning based upon the time that the test composition was administered on Day 0. These follow-on measurements were taken at 4-hour intervals through a 12 hour evaluation period (4 measurements). The time of use of any concomitant (supplemental) medications was also noted during this 4-day evaluation.

As can be seen by reviewing the results of the Incision Site Pain Scores test depicted in FIG. 6, both subgroups that received the SAIB/BA/bupivacaine test compositions (subgroups 1 and 2) displayed lower mean VAS scores at all times throughout the test as compared with the group that received the Marcain® test composition (subgroup 3). These results demonstrate that the compositions of the present invention provide sustained local anesthesia at the incision wound site with a duration of at least about 36 to 48 hours after administration to the subject. Patients for Cohort 3 will be divided into 2 treatment subgroups. The first subgroup will receive 7.5 mL total volume injections of the SAIB/BA/bupivacaine composition (containing 958 mg bupivacaine), administered as two trailing subcutaneous injections along each side of the surgical wound (0.75 mL/cm along a suggested 5 cm total length incision wound) with 10 mL Marcain® (0.5% Bupivacaine-HCl) infiltrated into the incision wound (including subfascial) prior to wound closure to yield a total of 1,008 mg bupivacaine administered per patient. The second subgroup will receive 7.5 mL total volume injections of the Marcain® (0.5% Bupivacaine-HCl) composition administered as two trailing subcutaneous injections along each side of the surgical wound (0.75 mL/cm along a suggested 5 cm total length incision wound) along with 10 mL Marcain® infiltrated into the incision wound (including subfascial) prior to wound closure to yield a total of 87.5 mg bupivacaine administered per patient.

Anesthetic/analgesic effect will be assessed using Time to First Supplemental Analgesic Medication, and Total Supplemental Analgesic Medication Consumption (over the course of 4 days) tests. Plasma bupivacaine concentration will be measured periodically throughout the course of the study, particularly through the first 24 hours to assess the magnitude of early bupivacaine release from the SAIB controlled release composition. It is expected that the higher dose SAIB/BA/Bupivacaine controlled release compositions prepared according to the present invention will provide similar or even greater efficacy results as compared with those of the Cohort 2 test subjects.

The present invention having been thus described, variations and modifications thereof as would be apparent to those of skill in the art will be understood to be within the scope of the appended claims.

What is claimed is:

1. A method for providing sustained local anesthesia by administering to a subject a composition comprising:
   about 66% by weight sucrose acetate isobutyrate (SAIB) liquid carrier material relative to the total weight of the composition;
   about 12% by weight bupivacaine relative to the total weight of the composition; and
   about 22% by weight benzyl alcohol (BA) relative to the total weight of the composition,
   wherein after administration the bupivacaine is released from said composition for a period of at least 24 hours in an amount sufficient to provide sustained local anesthesia.

2. The method of claim 1, wherein said composition is administered to a surgical wound.

3. The method of claim 2, wherein said composition is administered into and/or adjacent to the surgical wound.

4. The method of claim 2, wherein said composition is administered by pouring.

5. The method of claim 1, wherein said subject is a human patient undergoing surgical inguinal hernia repair or an appendectomy.

6. The method of claim 1, wherein said composition is used to treat post-operative pain.

7. The method of claim 1, wherein the bupivacaine is present in the composition in free base form.

8. The method of claim 1, wherein administration of said composition provides sustained local anesthesia for a period of at least about 48 hours.

9. The method of claim 1, wherein administration of said composition provides sustained local anesthesia for a period of at least about 72 hours.

* * * * *